(12) United States Patent
Kim

(10) Patent No.: US 11,119,063 B2
(45) Date of Patent: Sep. 14, 2021

(54) APPARATUS AND METHOD MEASURING BIOIMPEDANCE AND IMPEDANCE

(71) Applicant: Samsung Electronics Co., Ltd., Suwon-si (KR)

(72) Inventor: JongPal Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 165 days.

(21) Appl. No.: 16/375,899

(22) Filed: Apr. 5, 2019

(65) Prior Publication Data
US 2019/0383760 A1  Dec. 19, 2019

(30) Foreign Application Priority Data

Jun. 19, 2018 (KR) .................. 10-2018-0070409
Nov. 13, 2018 (KR) .................. 10-2018-0139270

(51) Int. Cl.
*G01N 27/06* (2006.01)
*G01N 27/02* (2006.01)
*A61B 5/053* (2021.01)

(52) U.S. Cl.
CPC ........... *G01N 27/026* (2013.01); *A61B 5/053* (2013.01)

(58) Field of Classification Search
CPC ....... A61B 5/053; A61B 5/725; A61B 5/7225; A61B 5/703; A61B 5/7203; A61B 5/0537; A61B 5/0535; A61B 5/242; A61B 5/0809; A61B 90/06; G01N 27/02; G01N 27/026; G01R 27/02; G01R 27/06; G01R 20/26; G01R 1/30

See application file for complete search history.

(56) References Cited

U.S. PATENT DOCUMENTS

| | | | | |
|---|---|---|---|---|
| 7,391,257 | B1* | 6/2008 | Denison | H03F 3/45183 330/9 |
| 8,909,333 | B2* | 12/2014 | Rossi | A61B 5/0537 600/547 |
| 9,615,744 | B2* | 4/2017 | Denison | H03F 3/45192 |
| 10,010,262 | B2* | 7/2018 | Kim | G01R 27/14 |
| 10,141,918 | B2* | 11/2018 | Kim | G11C 27/026 |

(Continued)

FOREIGN PATENT DOCUMENTS

| CN | 103475343 B | 1/2016 |
|---|---|---|
| CN | 104267244 B | 3/2017 |

(Continued)

OTHER PUBLICATIONS

Extended European Search Report dated Oct. 23, 2019 in corresponding European Patent Application No. 19173842.6 (6 pages in English).

*Primary Examiner* — Vinh P Nguyen
(74) *Attorney, Agent, or Firm* — NSIP Law

(57) ABSTRACT

An impedance measuring apparatus and method is disclosed. The impedance measuring apparatus includes one or more capacitors configured to receive an induced signal determined by an impedance of a measurement target, a controller configured to output a control signal to selectively turn a switch on or off based on whether a voltage value of the induced signal is included in a threshold range, and the switch configured to determine whether to set, to be a reference voltage value, a voltage value of a capacitor voltage signal output from the one or more capacitors based on the control signal.

22 Claims, 18 Drawing Sheets

(56) References Cited

U.S. PATENT DOCUMENTS

| | | | |
|---|---|---|---|
| 10,432,180 B2* | 10/2019 | Kim | ................. H03K 5/003 |
| 2009/0251126 A1 | 10/2009 | Ishino et al. | |
| 2015/0200637 A1* | 7/2015 | Ko | ................. H03F 1/0277 |
| | | | 330/9 |
| 2016/0015290 A1 | 1/2016 | Kim et al. | |
| 2016/0158200 A1 | 6/2016 | Hewawasam et al. | |
| 2017/0086702 A1 | 3/2017 | Kim et al. | |
| 2017/0126216 A1 | 5/2017 | Kim | |

FOREIGN PATENT DOCUMENTS

| | | | |
|---|---|---|---|
| EP | 0 977 355 A2 | 2/2000 |
| JP | 2004-48638 A | 2/2004 |
| JP | 5067442 B2 | 11/2012 |
| JP | 5402947 B2 | 1/2014 |
| KR | 10-2016-0098016 A | 8/2016 |

* cited by examiner

APPARATUS AND METHOD MEASURING BIOIMPEDANCE AND IMPEDANCE

This application claims the benefit under 35 USC § 119(a) of Korean Patent Application No. 10-2018-0070409 filed on Jun. 19, 2018, and Korean Patent Application No. 10-2018-0139270 filed on Nov. 13, 2018, in the Korean Intellectual Property Office, the entire disclosures of which are incorporated herein by reference for all purposes.

BACKGROUND

1. Field

The following description relates to impedance measuring technology.

2. Description of Related Art

A body consists of biological tissues having various electrical properties. A biological tissue may be conductive through ions and the like that may transport electric charges. Based on where a biological tissue is in a body, biological tissues may have different conductivities. For example, a biological tissue such as muscles may have characteristics of a conductor through which current may flow, whereas a biological tissue such as bones may have characteristics of a nonconductor that impedes current flow. A biological tissue may also have an electrical property of resistance or reactance. A portion of biological tissues may transfer a high-frequency input signal through an ohmic method, and another portion of the biological issues may transfer a low-frequency input signal through a capacitive method. To measure an impedance of a biological tissue, a minute alternating current may be applied to the biological tissue and an alternating voltage may be measured in response to the alternating current.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an impedance measuring apparatus includes one or more capacitors configured to receive an induced signal determined by an impedance of a measurement target, a controller configured to output a control signal to selectively turn a switch on or off based on whether a voltage value of the induced signal is included in a threshold range, and the switch configured to determine whether to set, to be a reference voltage value, a voltage value of a capacitor voltage signal output from the one or more capacitors based on the control signal.

In response to the voltage value of the induced signal being in the threshold range, the controller may output a first control signal to turn on the switch. In response to the voltage value of the induced signal being out of the threshold range, the controller may output a second control signal to turn off the switch.

The controller may include a comparator configured to receive a first threshold voltage value and a second threshold voltage value to define the voltage value of the induced signal and the threshold range, and compare the voltage value of the induced signal to each of the first threshold voltage value and the second threshold voltage value.

A first terminal of the switch may be connected to the one or more capacitors, and a second terminal of the switch may be connected to a terminal configured to provide the reference voltage value.

The impedance measuring apparatus may further include a signal processor configured to perform signal processing on the capacitor voltage signal transferred from a node to which the switch and the one or more capacitors are connected.

The signal processor may include a demodulator configured to adjust a phase of the capacitor voltage signal transferred to an input terminal of the signal processor, a peak detector configured to detect a peak from a demodulated voltage signal output from the demodulator, and a low-pass filter (LPF) configured to perform low-pass filtering on a peak-detected voltage signal output from the peak detector based on the detected peak.

The signal processor may further include an amplifier disposed between the node and the demodulator and configured to amplify the capacitor voltage signal transferred from the node.

The signal processor may further include an analog-to-digital converter (ADC) configured to convert an input analog voltage signal to a digital signal.

The impedance measuring apparatus may further include a current source configured to supply a current of a predefined frequency to the measurement target.

The impedance measuring apparatus may further include a high-pass filter (HPF) configured to perform high-pass filtering on the induced signal determined by the impedance of the measurement target.

The measurement target may be a biological body.

In another general aspect, an impedance measuring apparatus includes one or more capacitors configured to receive an induced signal determined by an impedance of a measurement target, a controller configured to output a control signal to selectively turn a switch on or off based on whether a voltage value of the induced signal is included in a threshold range and control whether to hold the control signal, and the switch configured to determine whether to set, to be a reference voltage value, a voltage value of a capacitor voltage signal output from the one or more capacitors based on the control signal.

The controller may include a control signal adjuster configured to output a control signal in response to an input signal, and hold the output control signal irrespective of an input signal during a predetermined time interval.

In still another general aspect, an impedance measuring apparatus includes one or more capacitors configured to receive an induced signal determined by an impedance of a measurement target, a controller configured to output a control signal to selectively turn a switch on or off based on whether a voltage value of the induced signal is included in a threshold range and control whether to hold the control signal, the switch configured to determine whether to set, to be a reference voltage value, a voltage value of a capacitor voltage signal output from the one or more capacitors based on the control signal, and a threshold range determiner configured to determine the threshold range based on whether the capacitor voltage signal output from the one or more capacitors satisfies a preset condition.

In response to the capacitor voltage signal output from the one or more capacitors being out of the threshold range, the threshold range determiner may increase the threshold range by a unit interval, and determine whether the capacitor voltage signal output from the one or more capacitors is in the increased threshold range.

In response to the capacitor voltage signal output from the one or more capacitors being out of a first set range, the threshold range determiner may increase the threshold range. In response to the capacitor voltage signal output from the one or more capacitors being in a second set range, the threshold range determiner may decrease the threshold range.

The impedance measuring apparatus may further include a signal processor configured to perform signal processing on a voltage signal transferred from a node to which the switch and the one or more capacitors are connected.

In yet another general aspect, an impedance measuring method includes receiving an induced signal determined by an impedance of a measurement target through a first terminal of one or more capacitors, determining whether to set a voltage value of a voltage signal output from a second terminal of the one or more capacitors to be a reference voltage value based on whether a voltage value of the induced signal is included in a threshold range, and outputting a voltage signal of the second terminal of the one or more capacitors based on a result of the determining.

The determining may include comparing the voltage value of the induced signal to the threshold range, and controlling a switch connected to the second terminal of the one or more capacitors based on a result of the comparing.

The controlling may include outputting a first control signal to turn on the switch in response to the voltage value of the induced signal being in the threshold range, and outputting a second control signal to turn off the switch in response to the voltage value of the induced signal being out of the threshold range.

The impedance measuring method may further include performing signal processing on the voltage signal of the second terminal of the one or more capacitors.

The performing of the signal processing may include amplifying the voltage signal of the second terminal of the one or more capacitors.

The performing of the signal processing may include adjusting a phase of the voltage signal of the second terminal of the one or more capacitors.

The performing of the signal processing may include detecting a peak from the voltage signal of the second terminal of the one or more capacitors.

The performing of the signal processing may include performing low-pass filtering on a voltage signal output from the peak detector based on the detected peak.

The measurement target may be a biological body.

In another general aspect, an impedance measuring method to be performed by an impedance measuring apparatus includes receiving, through a first terminal of a capacitor, an induced signal to be determined by an impedance of a measurement target, determining whether to set a voltage value of a capacitor voltage signal output from a second terminal of the capacitor to be a reference voltage value based on whether a voltage value of the induced signal is included in a threshold range, and outputting the capacitor voltage signal of the second terminal of the capacitor based on a result of the determining.

The determining may include comparing the voltage value of the induced signal to the threshold range, and controlling a switch connected to the second terminal of the capacitor based on a result of the comparing.

The controlling may include in response to the voltage value of the induced signal being included in the threshold range, outputting a first control signal to turn on the switch, and in response to the voltage value of the induced signal not being included in the threshold range, outputting a second control signal to turn off the switch.

The impedance measuring method may further include performing signal processing on the capacitor voltage signal of the second terminal of the capacitor.

The performing of the signal processing may include amplifying the capacitor voltage signal of the second terminal of the capacitor.

The performing of the signal processing may include adjusting a frequency band of the capacitor voltage signal of the second terminal of the capacitor.

The performing of the signal processing may include detecting a peak from the capacitor voltage signal of the second terminal of the capacitor.

The performing of the signal processing may include performing low-pass filtering on a peak-detected voltage signal output from a peak detector based on the detected peak.

In another general aspect, an impedance measuring apparatus includes a switch, one or more capacitors, and a controller. The one or more capacitors is connected to the switch, and configured to receive an induced signal determined by an impedance of a biological body. The controller is connected to the switch, and configured to output a control signal to selectively turn a switch on or off based on whether a voltage value of the induced signal is within a threshold range. The switch is configured to determine whether to set, to be a reference voltage value, a voltage value of a capacitor voltage signal output from the one or more capacitors based on the control signal.

The controller may include a comparator configured to: receive a first threshold voltage value and a second threshold voltage value to define the voltage value of the induced signal and the threshold range, and compare the voltage value of the induced signal to each of the first threshold voltage value and the second threshold voltage value.

The controller may further include a control signal adjuster disposed between the comparator and the switch, configured to output a control signal in response to an input signal, and hold the output control signal irrespective of an input signal during a predetermined time interval.

The impedance measuring apparatus may further include a signal processor connected to the switch, and configured to process a voltage signal transferred from the switch.

The signal processor may include an amplifier having an input terminal connected to the node, and configured to amplify the voltage signal transferred from the node; a demodulator connected to the amplifier, and configured to adjust a frequency band of the amplified voltage signal; a peak detector connected to the demodulator, and configured to detect a peak from a demodulated voltage signal output from the demodulator; and a low-pass filter (LPF) connected to the peak detector, and configured to filter a peak-detected voltage signal output from the peak detector based on the detected peak.

In another general aspect, an impedance measuring method receiving, by one or more capacitors, an induced signal determined by an impedance of a measurement target; outputting, by a controller, a control signal to selectively turn a switch on or off based on whether a voltage value of the induced signal is included in a threshold range; and determining whether to set, to be a reference voltage value, a voltage value of a capacitor voltage signal output from the one or more capacitors based on the control signal.

Other features and aspects will be apparent from the following detailed description, the drawings, and the claims.

Figure 1:
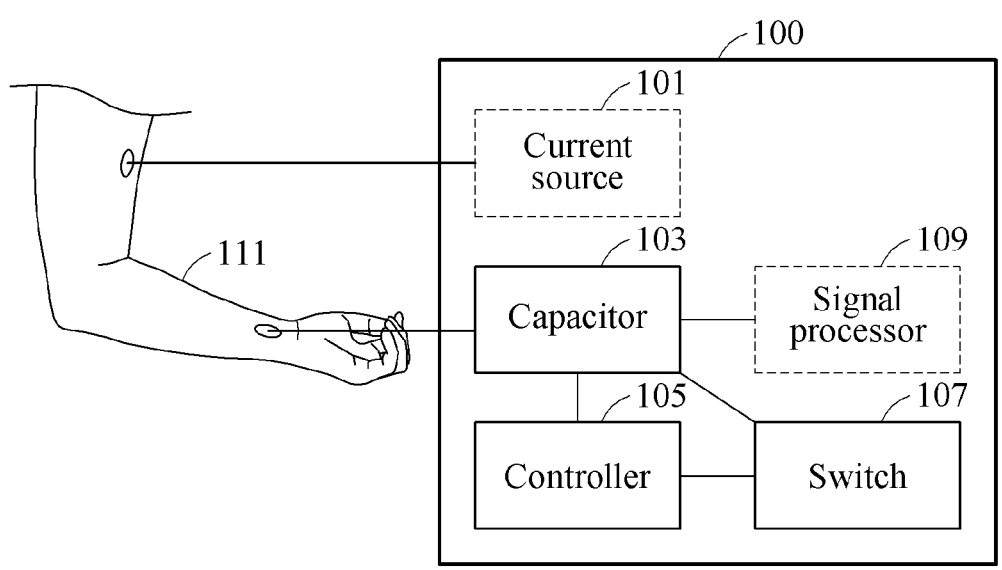
FIG. 1 is a diagram illustrating an example of a configuration of an impedance measuring apparatus.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known after an understanding of the disclosure of this application may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween. As used herein, the term "and/or" includes any one and any combination of any two or more of the associated listed items.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Unless otherwise defined, all terms, including technical and scientific terms, used herein have the same meaning as commonly understood by one of ordinary skill in the art to which this disclosure pertains and based on an understanding of the disclosure of the present application. Terms, such as those defined in commonly used dictionaries, are to be interpreted as having a meaning that is consistent with their meaning in the context of the relevant art and the disclosure of the present application, and are not to be interpreted in an idealized or overly formal sense unless expressly so defined herein.

Also, in the description of example embodiments, detailed description of structures or functions that are thereby known after an understanding of the disclosure of the present application will be omitted when it is deemed that such description will cause ambiguous interpretation of the example embodiments.

FIG. 1 is a diagram illustrating an example of a configuration of an impedance measuring apparatus.

Referring to FIG. 1, an impedance measuring apparatus 100 may measure an impedance of a body 111, or a bioimpedance. The impedance measuring apparatus 100 may apply a current signal to the body 111 and measure a voltage signal from the body 111. By analyzing the measured voltage signal using the applied current signal and a characteristic determined by the impedance of the body 111, the impedance of the body 111 may be estimated. Based on the estimated impedance, a state of the body 111, such as, for example, a ratio of a body tissue such as body fat and the like, may then be estimated. Herein, measurement of such an impedance of a body, or a bioimpedance, may be performed relatively inexpensively and for a relatively shorter amount of time, compared to X-ray measurement, ultrasonic measurement, or magnetic resonance-based measurement, for example.

The impedance measuring apparatus 100 may apply an input current to the body 111 through a first electrode pair attached to the body 111 in a contact or contactless manner, and receive an induced signal through a second electrode pair. Herein, as a non-limiting example, the first electrode pair and the second electrode pair may be identical to each other. For example, the impedance measuring apparatus 100 may apply current to the body 111 through the first electrode pair attached to a right arm and a left arm, and receive an induced signal through the same first electrode pair or through the second electrode pair attached, separately from the first electrode pair, to the right arm and left arm. A portion of the body 111 to which the first electrode pair and the second electrode pair are attached is not limited to the examples described in the foregoing, and the first electrode pair and the second electrode pair may be attached to various portions of a user's body. In this example, the induced signal may be a signal obtained by measuring a voltage that is induced in response to the applied current. The induced signal may also be referred to as an output signal or a measurement result signal.

In an example, information associated with the current applied to the body 111 by a current source 101 may be predetermined. For example, information associated with the magnitude, the frequency, and the waveform of the current applied to the body 111 may be predefined information. The impedance measuring apparatus 100 may obtain, from the induced signal, information associated with a voltage determined by the current applied to the body 111. The impedance of the body 111 may be calculated based on the predetermined information associated with the current and the information associated with the voltage obtained from the induced signal. For example, the impedance of the body 111 may be calculated from a magnitude of the current and a magnitude of the voltage based on the ohm's law. A phase of the impedance may be calculated based on a difference between a time at which a peak of the applied current is indicated and a time at which a peak of the voltage of the induced signal is indicated.

Herein, an impedance may include a static signal component and a dynamic signal component. In a case in which the induced signal has a great static signal component including a direct current (DC) component, the impedance may also have a great proportion of the static signal component. For example, a ratio of the dynamic signal component to the static signal component may be 1/10 to 1/100. The dynamic signal component may correspond to a change occurring in response to respiration, stimulation, or the like, and be a target signal of interest. The static signal component may be irrelevant to stimulation and not be a target signal of interest. A dynamic signal component of the induced signal may be necessary for measuring the impedance, and thus a high-resolution analog-to-digital converter (ADC) may be needed when the induced signal has a great proportion of the static signal component. When using an amplifier with a set maximum input voltage, the amplifier may be easily saturated due to the static signal component of the induced signal, and thus the measurable impedance may be limited.

In an example, the impedance measuring apparatus 100 may perform signal processing only on a dynamic signal component, which is a target signal of interest, by removing a static signal component, which is not a target signal of interest, from the induced signal. Thus, the impedance measuring apparatus 100 may normally perform signal processing also on an induced signal with a wider amplitude without the saturation.

Referring to Equation 1 represented in terms of impedance, compensated impedance information $Z_{sense\_comp}$ may be obtained by removing a predetermined amount of compensation impedance $Z_{comp}$ from impedance information $Z_{sense}$ included in an induced signal. In the compensated impedance information $Z_{sense\_comp}$, a ratio of impedance information $\Delta Z$ corresponding to a dynamic signal component to basic impedance information $Z_0$ may considerably increase. In Equation 1, $Z_0 > Z_{comp}$.

$$Z_{sense\_comp} = Z_{sense} - Z_{comp} = Z_0 + \Delta Z - Z_{comp} \qquad \text{Equation 1:}$$

Thus, the impedance measuring apparatus 100 includes a capacitor 103, a controller 105, and a switch 107. The capacitor 103 may receive an induced signal to be determined based on the impedance of a measurement target. The capacitor 103 may remove a DC component from the induced signal. Here, capacitor 103 represents one or more capacitors.

The controller 105 may output a control signal to turn on or off the switch 107 based on whether a voltage value of the induced signal is included in a threshold range. In response to the voltage value of the induced signal being in the threshold range, the controller 105 may output a first control signal to turn on the switch 107. In response to the voltage value of the induced signal being out of the threshold range, the controller 105 may output a second control signal to turn off the switch 107.

The switch 107 may determine whether to set, to be a reference voltage value, a voltage value of a voltage signal output from the capacitor 103 based on the control signal. Herein, one end of the switch 107 is connected to a reference voltage, and thus the voltage value of the voltage signal output from the capacitor 103 may be set to be the reference voltage value when the switch 107 is turned on in response to the first control signal. When the switch 107 is turned off in response to the second control signal, the voltage value of the voltage signal output from the capacitor 103 may be transferred to an output end.

In an example, the impedance measuring apparatus 100 includes the current source 101 according to examples, while in another example, the impedance measuring apparatus 100 does not include the current source 101. In the example where the impedance measuring apparatus 100 includes the current source 101, the impedance measuring apparatus 100 may apply an input current to the body 111 through the current source 101. In a case in which the impedance measuring apparatus 100 does not include the current source 101, the impedance measuring apparatus 100 may measure a voltage induced by the input current that is applied to the body 111 through the current source 101 provided outside the impedance measuring apparatus 100. In such cases, information associated with a magnitude and a waveform of the input current is predetermined.

The impedance measuring apparatus 100 may further include a signal processor 109.

The signal processor 109 may perform, on the induced signal, amplification, demodulation, peak detection, filtering, and analog-to-digital conversion, or a combination thereof. For example, the signal processor 109 may measure a phase of the impedance by demodulating a frequency band of the induced signal, or detecting a peak of the induced signal and comparing the detected peak and a peak of the applied input current. The signal processor 109 may also perform filtering-based signal smoothness and digital signal conversion to provide a voltage value that is suitably processed for impedance measurement. Herein, it is noted that use of the term 'may' with respect to an example or embodiment, e.g., as to what an example or embodiment may include or implement, means that at least one example or embodiment exists where such a feature is included or implemented while all examples and embodiments are not limited thereto.

Figure 2:
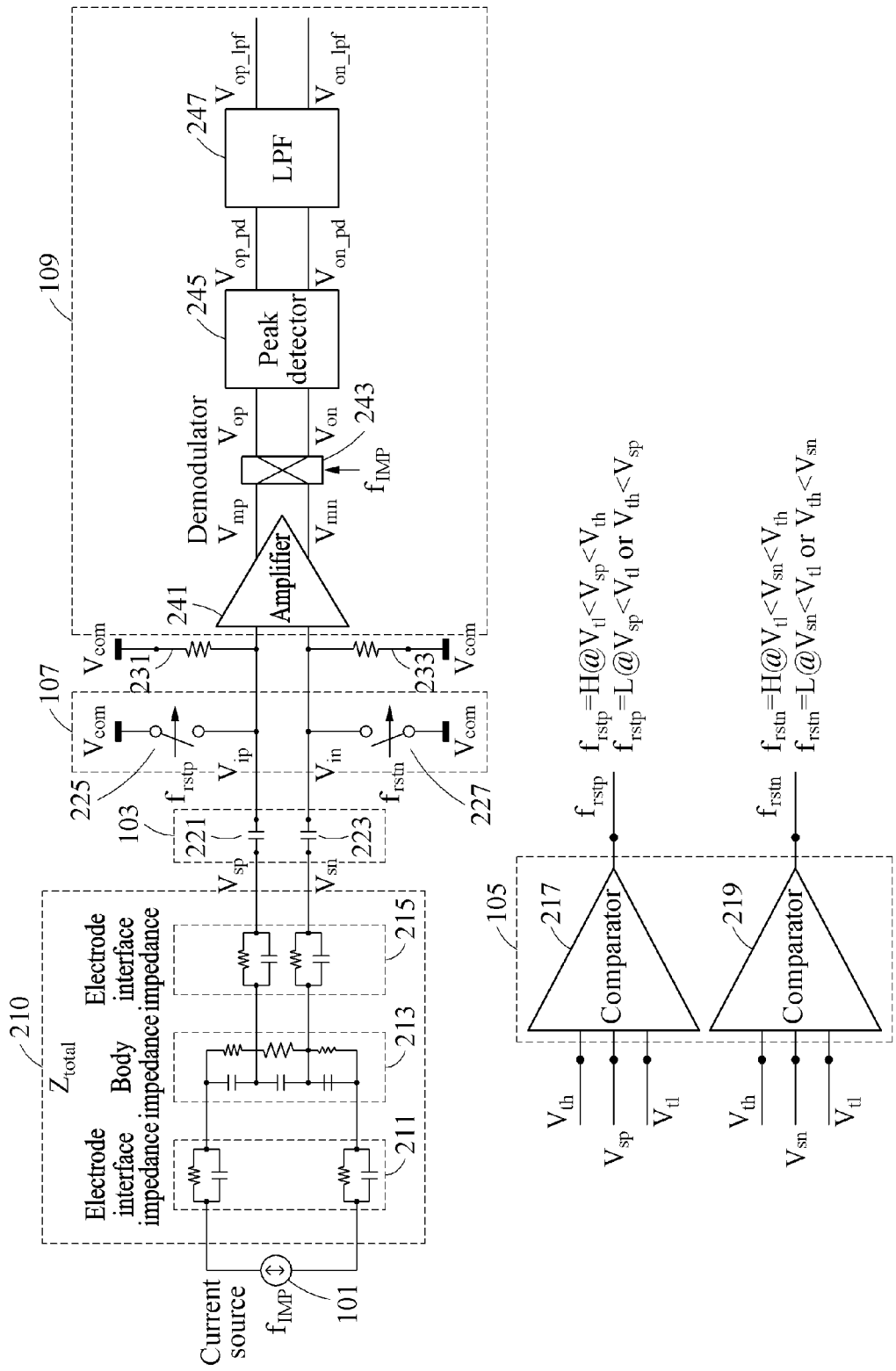
FIG. 2 is a diagram illustrating an example of a detailed configuration of an impedance measuring apparatus.

FIG. 2 is a diagram illustrating an example of a configuration of an impedance measuring apparatus.

Referring to FIG. 2, a total impedance 210 includes a body impedance 213, and an electrode interface impedance 211 and an electrode interface impedance 215. In this example, an impedance of a body may be modeled as the body impedance 213. The body impedance 213 may be selected from among various models, or experimentally modeled. Each of an input electrode of a current source 101 and an output electrode from which an induced signal is output may also have an impedance component. The electrode interface impedance 211 may indicate an impedance of the input electrode of the current source 101, and the electrode interface impedance 215 may indicate an impedance of the output electrode from which the induced signal is output. Below, explanations of FIG. 2 will be made with reference to the impedance measuring apparatus 100 of FIG. 1 for explanation purposes, thus, noting that examples are not limited thereto.

Thus, in an example, the impedance measuring apparatus 100 of FIG. 1 includes a capacitor 103, a switch 107, and a controller 105. The controller 105 includes comparators 217 and 219. The current source 101 may be included in the impedance measuring apparatus 100, or present as an external device. The current source 101 may supply current of a predefined frequency to a measurement target.

The current source 101 applies an input current to the body. The input current is a sinusoidal wave of a frequency $f_{imp}$. The input current passes through the body and is then output as induced signals $V_{sp}$ and $V_{sn}$. The comparators 217 and 219 receive, as inputs, a first threshold voltage value $V_{th}$ and a second threshold voltage value $V_{th}$ to define voltage values of the induced signals $V_{sp}$ and $V_{sn}$ and a threshold range. The threshold range of the comparators 217 and 219 may be set based on the first threshold voltage value $V_{th}$ and the second threshold voltage value $V_{th}$. The induced signal $V_{sp}$ is input to the comparator 217. The comparators 217 and 219 compare the voltage values of the induced signals $V_{sp}$ and $V_{sn}$ to each of the first threshold voltage value $V_{th}$ and the second threshold voltage value $V_{th}$.

In response to the voltage value of the induced signal $V_{sp}$ being between the first threshold voltage value $V_{th}$ and the second threshold voltage value $V_{th}$, a control signal $f_{rstp}$ of the comparator 217 may be set to be high H. In response to the voltage value of the induced signal $V_{sp}$ being greater than the first threshold voltage value $V_{th}$ or being less than the second threshold voltage value $V_{th}$, the control signal $f_{rstp}$ of the comparator 217 may be set to be low L. Herein, H and L indicate logical values. The induced signal $V_{sn}$ is input to the comparator 219. In response to the voltage value of the induced signal $V_{sn}$ being between the first threshold voltage value $V_{th}$ and the second threshold voltage value $V_{th}$, a control signal $f_{rstp}$ of the comparator 219 may be set to be H. In response to the voltage value of the induced signal $V_{sn}$ being greater than the first threshold voltage value $V_{th}$ or being less than the second threshold voltage value $V_{th}$, the control signal $f_{rstp}$ of the comparator 219 may be set to be L.

As a non-limiting example, the capacitor 103 includes capacitors 221 and 223 respectively corresponding to the induced signals $V_{sp}$ and $V_{sn}$ which are differential signals. The capacitors 221 and 223 remove DC components from the induced signals $V_{sp}$ and $V_{sn}$, respectively, and output signals $V_{ip}$ and $V_{in}$. The capacitors 221 and 223 are connected to a reference voltage $V_{com}$ indicated by 231 and 233, and thus the reference voltage $V_{com}$ may be set to be a central value of the output signals $V_{ip}$ and $V_{in}$. Herein, the reference voltage $V_{com}$ may form a common voltage of the differential signals.

The switch 107 includes switches 225 and 227 respectively corresponding to the induced signals $V_{sp}$ and $V_{sn}$ which are the differential signals. A first terminal of each of the switches 225 and 227 is connected to the capacitors 221 and 223, respectively. A second terminal of each of the switches 225 and 227 is connected to a reference voltage source configured to provide the reference voltage $V_{com}$. The switches 225 and 227 are set to be turned on and turned off based on different controls of the control signal $f_{rstp}$. As a non-limiting example, in response to the control signal $f_{rstp}$ being H, the switches 225 and 227 may be set to be on, and the output signals $V_{ip}$ and $V_{in}$ may be set to be the reference voltage $V_{com}$ irrespective of the induced signals $V_{sp}$ and $V_{sn}$, while in response to the control signal $f_{rstp}$ being L, the switches 225 and 227 may be set to be off, and the output signals $V_{ip}$ and $V_{in}$ may follow the induced signals $V_{sp}$ and $V_{sn}$ based on the reference voltage $V_{com}$.

Through the operations of the capacitor 103 and the switch 107 as described above, in an example, an impedance component of $Z_{comp}$ as represented by Equation 1 above may be removed from impedance components included in an induced signal.

In an example, the impedance measuring apparatus 100 further includes a signal processor 109. The signal processor 109 performs signal processing on voltage signals $V_{ip}$ and $V_{in}$ transferred from a node to which the switches 225 and 227 and the capacitors 221 and 223 are connected. The signal processor 109 may include an amplifier 241, a demodulator 243, a peak detector 245, and a low-pass filter (LPF) 247. According to an example, among these, the signal processor 109 may include: (a) only the amplifier 241; (b) only the amplifier 241 and the demodulator 243 connected to the amplifier 241; (c) only the amplifier 241 and the peak detector 245 connected to the amplifier 241; (d) the amplifier 241, the demodulator 243 connected to the amplifier 241, and the LPF 247 connected to the demodulator 243; (e) the amplifier 241, the peak detector 245 connected to the amplifier 241, and the LPF 247 connected to the peak detector 245; or (f) all of the amplifier 241, the demodulator 243 connected to the amplifier 241, the peak detector 245 connected to the demodulator 243, and the LPF 247 connected to the peak detector 245 as illustrated in FIG. 2.

Referring to the example (f) described above, the amplifier 241 amplifies the output signals $V_{ip}$ and $V_{in}$ to output signals $V_{mp}$ and $V_{mn}$. The amplifier 241 is disposed between the node and the demodulator 243, and amplifies the voltage signals $V_{mp}$ and $V_{in}$ transferred from the node. The demodulator 243 demodulates the voltage signals $V_{mp}$ and $V_{mn}$ to output signals $V_{op}$ and $V_{on}$. The peak detector 245 detects peaks of the voltage signals $V_{op}$ and $V_{on}$ output from the demodulator 243 to output signals $V_{op\_pd}$ and $V_{on\_pd}$. The LPF 247 performs low-pass filtering on the signals $V_{op\_pd}$ and $V_{on\_pd}$ to smooth the signals $V_{op\_pd}$ and $V_{on\_pd}$. The LPF 247 performs low-pass filtering on the voltage signals $V_{op\_pd}$ and $V_{on\_pd}$ output from the peak detector 245 based on the detected peaks. The LPF 247 may then output smoothed output signals $V_{op\_lpf}$ and $V_{on\_lpf}$.

In an example, the signal processor 109 may further include an ADC (not shown).

The ADC may be connected to a last component in an arrangement of each of the examples (a) through (f) as described above, and may receive an analog voltage signal output from the last component and convert the input analog voltage signal to a digital signal. For example, in the example (f), the ADC may perform analog-to-digital conversion on the output signals $V_{op\_lpf}$ and $V_{on\_lpf}$ which are analog signals output from the LPF 247 to generate a digital signal.

Figure 3A:
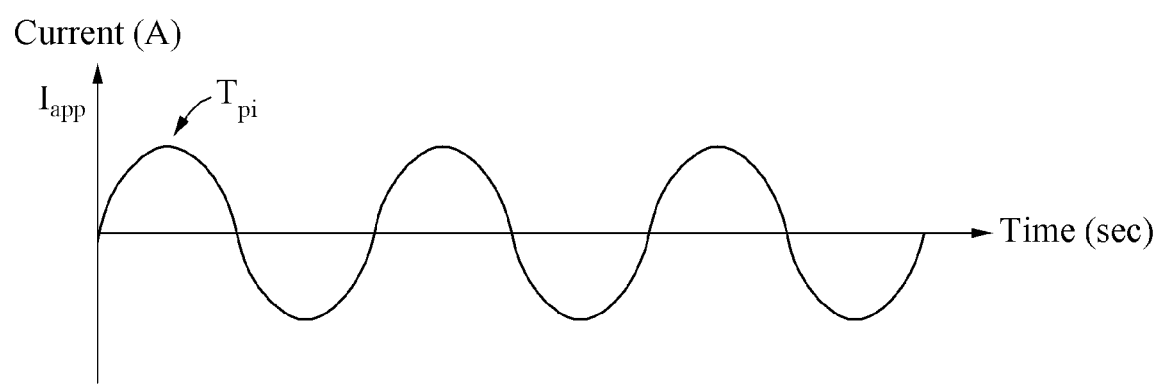
FIG. 3A is a graph illustrating an example of a current value of an input signal of a current source of an impedance measuring apparatus.

FIG. 3A is a graph illustrating an example of a current value of an input signal of a current source of an impedance measuring apparatus.

A portion of differential signals, for example, $V_{sp}$, $V_{mp}$, $V_{op}$, $V_{op\_pd}$, and $V_{op\_lpf}$ will be mainly described for convenience of description provided hereinafter with reference to FIGS. 3A through 3D. The description may also be applied to another portion of the differential signals, for example, $V_{sn}$, $V_{in}$, $V_{mn}$, $V_{on}$, $V_{on\_pd}$, and $V_{on\_lpf}$.

An input signal of a current source may include current of a waveform that varies on a periodic basis. For example, referring to FIG. 3A, current of an input signal of the current source may be of a sinusoidal wave. In this example, $T_{pi}$ indicates a point in time at which the current reaches its peak.

Figure 3B:
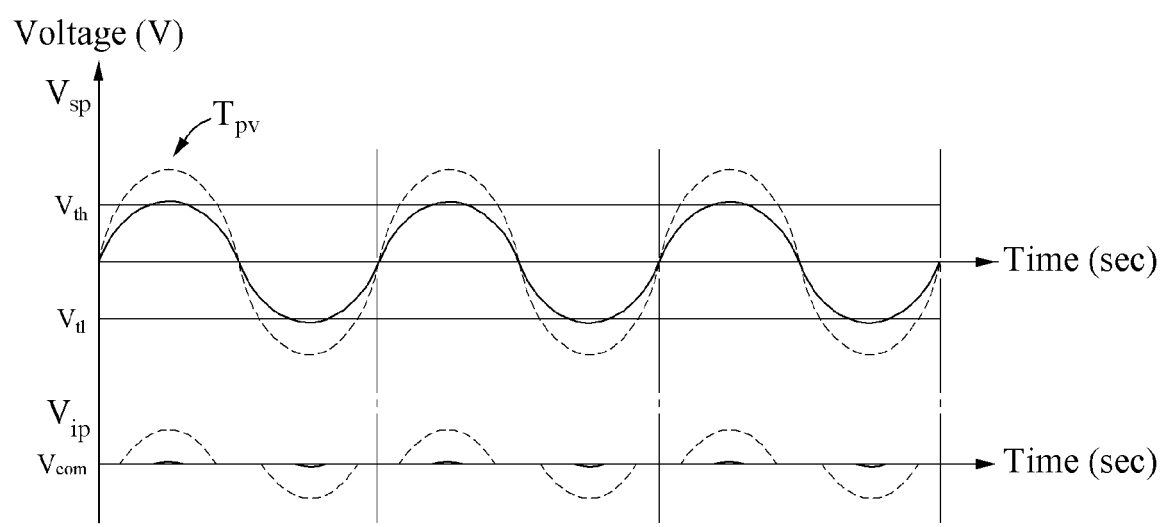
FIG. 3B is a graph illustrating an example of a voltage value of an induced signal of an impedance measuring apparatus and an example of a voltage value of a voltage signal output from a capacitor of the impedance measuring apparatus.

FIG. 3B is a graph illustrating an example of a voltage value of an induced signal of an impedance measuring apparatus and an example of a voltage value of a voltage signal output from a capacitor of the impedance measuring apparatus.

A biological tissue may have different conductivities and various electrical properties based on a region or a portion where it is, and thus an induced signal may have a magnitude and a phase that are different from those of an input signal $I_{app}$ of the current source. When the input signal $I_{app}$ of the current source passes through a body, an induced signal to be output may have an amplitude and a phase that are different from those of the input signal $I_{app}$ of the current source.

In the example of FIG. 3B, an induced signal $V_{sp}$ is illustrated. A first induced signal indicated by a broken line and a second induced signal indicated by a solid line as the input signal $I_{app}$ of the current source changes are also illustrated. The first induced signal and the second induced signal may have different amplitudes and phases from those of the input signal $I_{app}$ of the current source due to the influence of a measurement target, such as the target location of the body. Herein, a phase of an induced signal may be delayed from the phase of the input signal $I_{app}$ of the current source. For example, a point $T_{pv}$ in time at which the first induced signal reaches its peak, in FIG. 3B, may be different from a point $T_{pi}$ in time at which the input signal $I_{app}$ of the current source reaches its peak, in FIG. 3A.

An output signal $V_{ip}$ of a capacitor may have a waveform in which a static signal component, which is not a target signal of interest, is removed from the induced signal $V_{sp}$. By the operations of the capacitor and a switch, the output signal $V_{ip}$ may include only a dynamic signal component which is a target signal of interest.

In response to a voltage value of the induced signal $V_{sp}$ being included in a threshold range between $V_{th}$ and $V_{tl}$, a comparator may output a first control signal to turn on the switch. When the switch is turned on in response to the first control signal, a voltage value of a voltage signal output from the capacitor may be set to be a referenced voltage value $V_{com}$. Conversely, in response to the voltage value of the induced signal $V_{sp}$ being out of the threshold range, the comparator may output a second control signal to turn off the switch. When the switch is turned off in response to the second control signal, the voltage value of the voltage signal output from the capacitor may be transferred to an output terminal.

Thus, in response to the voltage value of the induced signal $V_{sp}$ being out of the threshold range between $V_{th}$ and $V_{tl}$, the output signal $V_{ip}$ may have a waveform that follows the induced signal $V_{sp}$ based on the reference voltage value $V_{com}$. In response to the voltage value of the induced signal $V_{sp}$ being in the threshold range between $V_{th}$ and $V_{tl}$, the voltage value may be set to be the reference voltage value $V_{com}$.

Figure 3C:
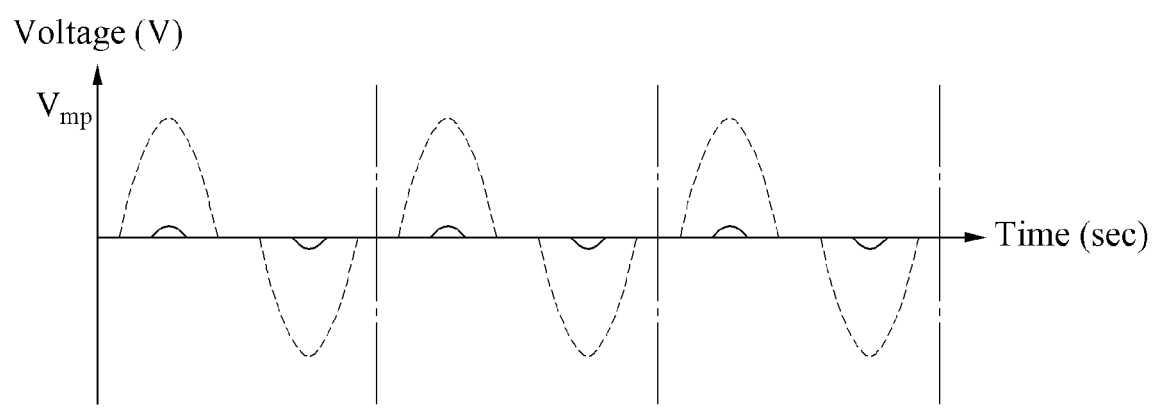
FIG. 3C is a graph illustrating an example of a voltage value output from an amplifier of an impedance measuring apparatus.

FIG. 3C is a graph illustrating an example of a voltage value output from an amplifier of an impedance measuring apparatus.

An output signal $V_{ip}$ of a capacitor may be input to an amplifier. Since an uninterested portion, noise, is removed from the output signal $V_{ip}$, the variation in amplitude of the output signal $V_{ip}$ may be relatively less compared to a case where signal processing is not performed by the capacitor and a switch. Thus, although, while the operating voltage of an amplifier is typically limited, the output signal $V_{ip}$ may be included in an operating range of the amplifier. Referring to FIG. 3C, the output signal $V_{ip}$ of FIG. 3B may be amplified by the amplifier. The variation in amplitude of an output signal $V_{mp}$ of the amplifier may be greater than the variation in amplitude of the output signal $V_{ip}$. The output signal $V_{mp}$ indicated by a broken line may correspond to the first induced signal also indicated by a broken line in the example of FIG. 3B, and the output signal $V_{mp}$ indicated by a solid line may correspond to the second induced signal also indicated by a solid line in the example of FIG. 3B.

Figure 3D:
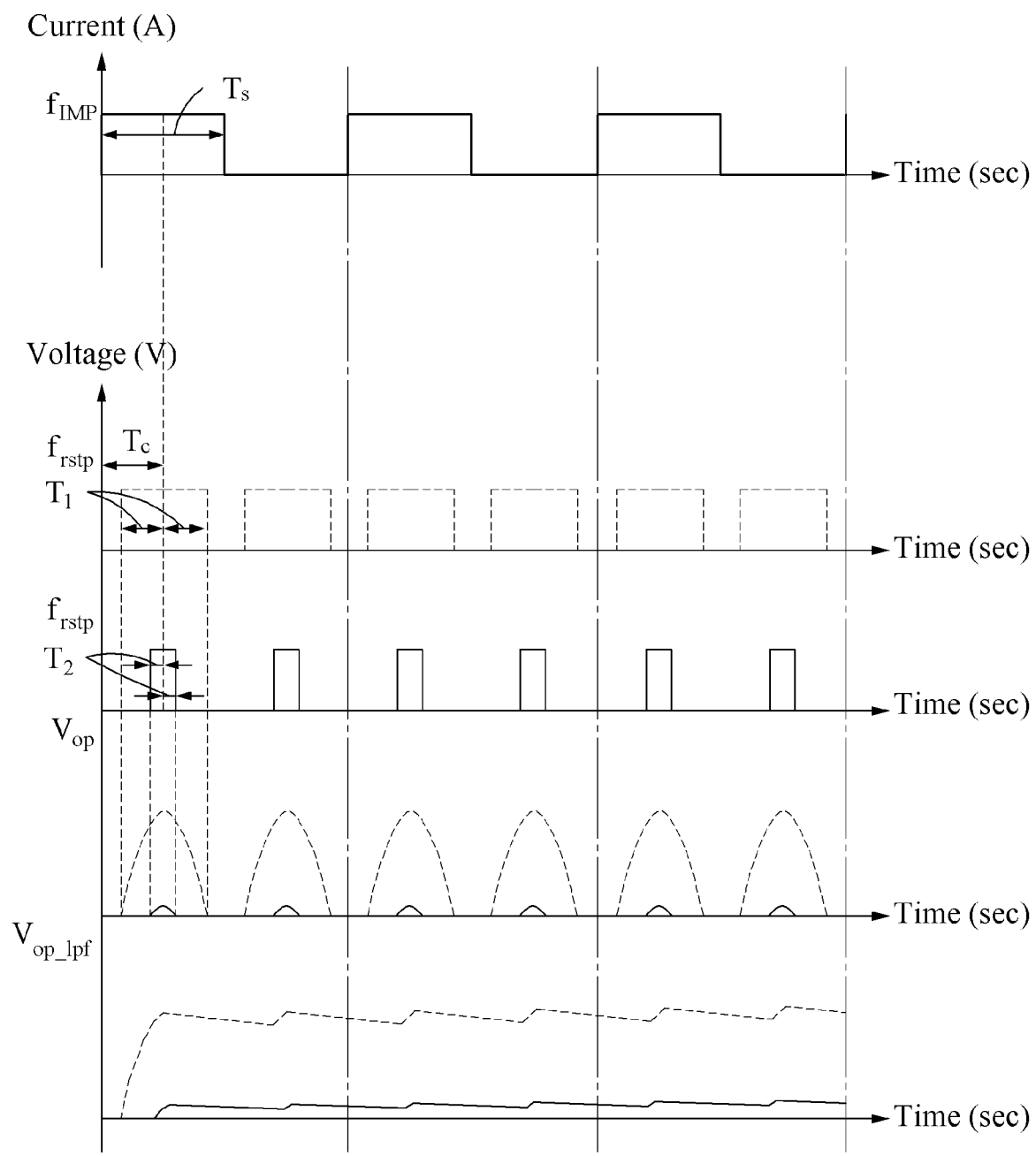
FIG. 3D is a graph illustrating examples of signals associated with a signal processor of an impedance measuring apparatus.

FIG. 3D is a graph illustrating examples of signals associated with a signal processor of an impedance measuring apparatus.

A demodulator may adjust a phase of the output signal $V_{mp}$ of FIG. 3C. The demodulator may reverse a waveform of the output signal $V_{mp}$ less than a center voltage value. An output signal $V_{op}$ of the demodulator may have a waveform in which a waveform greater than the center voltage value is periodically included.

A peak detector may detect a peak of the output signal $V_{op}$. A time at which the peak is detected may be identical to $T_{pv}$ in the example of FIG. 3B. The peak detector may detect a time at which the output signal $V_{op}$ reaches its peak, and a peak value. An LPF may smooth an output signal $V_{op\_pd}$ of the peak detector. The LPF may output a signal following a value that increases when a magnitude of an input signal increases. When the magnitude of the input signal decreases, the LPF may gradually decrease an output magnitude from a previous maximum magnitude. In the example of FIG. 3D, an output signal $V_{op\_lpf}$ of the LPF is illustrated An ADC may then convert, to a digital signal, the output signal $V_{op\_lpf}$ which is an analog signal.

An impedance measuring apparatus, such as the impedance measuring apparatus 100 of FIG. 1 as a non-limiting example, may calculate a phase of an impedance based on a peak of an applied current and a peak of a voltage of an induced signal. The impedance measuring apparatus may calculate the phase of the impedance based on a difference between a time $T_{pi}$ at which the current reaches its peak and a time $T_{pv}$ at which the induced signal reaches its peak. The impedance measuring apparatus may calculate the phase of the impedance based on Equation 2.

$$R_{ph} = \text{abs}(T_{pi} - T_{pv})/\Delta T_s/2 - \Delta T_c)/\Delta T_s$$

$$T_{pi} = \Delta T_s/2, \; T_{pv} = \Delta T_c \qquad \text{Equation 2}$$

In Equation 2, $\Delta T_s$ denotes a half period of a square wave current supplied from a current source. $R_{ph}$ may be calculated by dividing, by $\Delta T_s$, an absolute value of the difference between the time $T_{pi}$ at which the current reaches the peak and the time $T_{pv}$ at which the induced signal reaches the peak. Herein, $T_{pi} = \Delta T_s/2$ and $T_{pv} = \Delta T_c$, and thus $R_{ph}$ may be $0.5 - \Delta T_0/\Delta T_s$. The impedance measuring apparatus may determine that the impedance is close to a resistance component when $R_{ph}$ is closer to 0, and that the impedance is close to a capacitor component when $R_{ph}$ is closer to 0.5. Herein, $\Delta T_c$ may be calculated based on a time $\Delta T_1$ of a unit waveform of a control signal $f_{rstp}$ corresponding to a first induced signal, or a time $\Delta T_2$ of a unit waveform of a control signal $f_{rstp}$ corresponding to a second induced signal.

Figure 4:
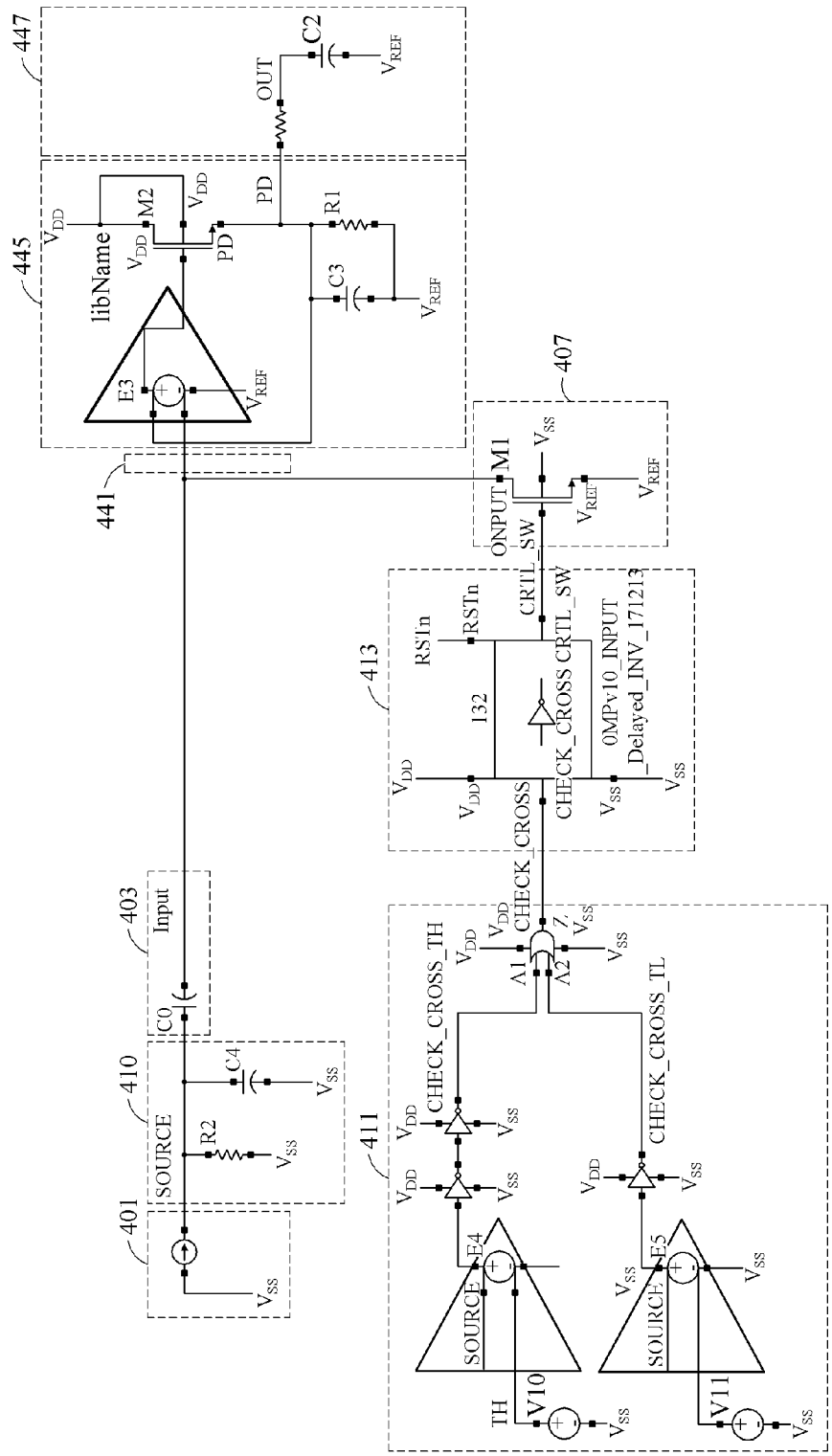
FIG. 4 is a diagram illustrating an example of a detailed configuration of an impedance measuring apparatus.

FIG. 4 is a diagram illustrating another example of a detailed configuration of an impedance measuring apparatus.

Referring to FIG. 4, an impedance measuring apparatus includes a capacitor 403, a controller, and a switch 407. The capacitor 403 may receive an induced signal determined by an impedance of a measurement target. The switch 407 may determine whether to set, to be a reference voltage value, a voltage value of a voltage signal output from the capacitor 403 based on a control signal. The controller may output a control signal to turn on or off the switch 407 based on whether the voltage value of the induced signal is included in a threshold range, and control whether to hold the control signal.

The controller includes a comparator 411 and a control signal adjuster 413. The comparator 411 may output the control signal to turn on or off the switch 407 based on whether the voltage value of the induced signal is included in the threshold range.

The control signal adjuster 413 may output an output value in response to a change in input signal, and maintain the output value without responding to a change in input for a preset amount of time after the output. Thus, the control signal adjuster 413 may prevent an oscillation that may be caused by feedback. The control signal adjuster 413 may also be referred to as an invert-and-hold inverter or an action-and-hold inverter.

The impedance measuring apparatus further includes a current source 401. The current source 401 may apply a preset current to a body. An impedance including a body impedance and an electrode interface impedance may be represented by a total impedance model 410.

The impedance measuring apparatus further includes a signal processor. The signal processor includes a peak detector 445 or an LPF 447. The signal processor further includes an amplifier, which may be disposed at a position 441 in the example of FIG. 4.

Figure 5:
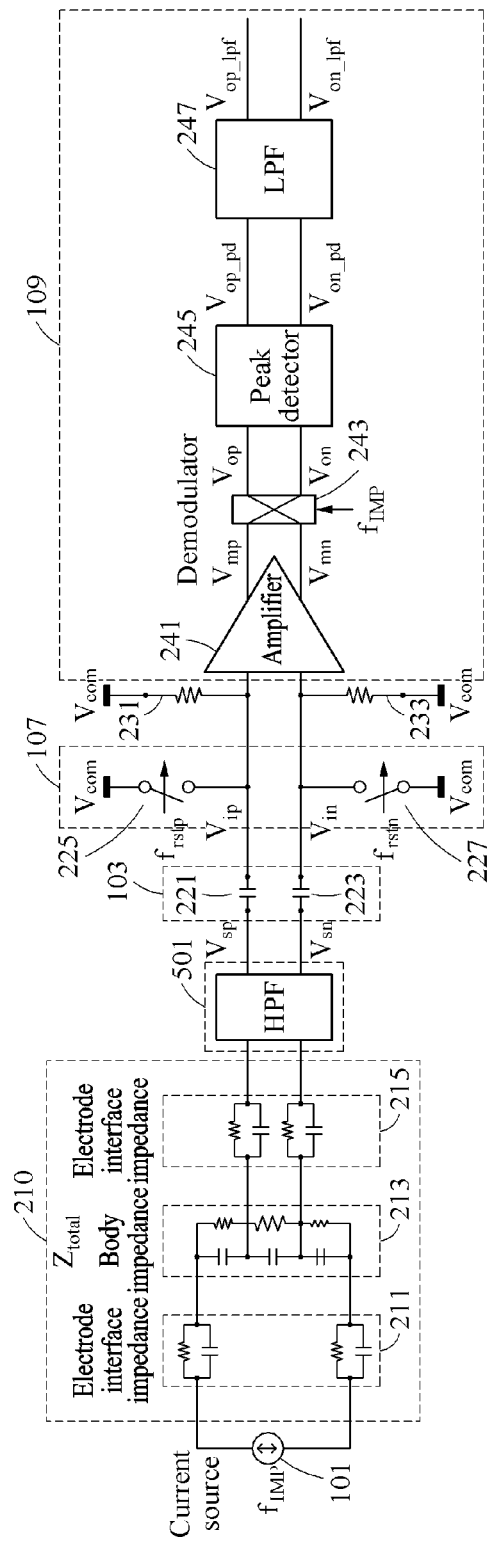
FIG. 5 is a diagram illustrating an example of a detailed configuration of an impedance measuring apparatus.

FIG. 5 is a diagram illustrating an example of a configuration of an impedance measuring apparatus.

Referring to FIG. 5, an impedance measuring apparatus includes a capacitor 103, a switch 107, a controller, and a high-pass filter (HPF) 501, for example. In an example, a current source 101 may be included in the impedance measuring apparatus, while in another example, the current source 101 is provided as an external device.

A body impedance 213 which is a measurement target may be included in a total impedance 210, and the total impedance 210 may include the body impedance 213, and an electrode interface impedance 211 and an electrode interface impedance 215.

The current source 101 applies an input current to a body. The input current may be a sinusoidal wave of a frequency $f_{IMP}$. The input current passes through the body, and outputs an induced signal. The induced signal may be input to the HPF 501.

The HPF 501 performs high-pass filtering on the induced signal. The HPF 501 outputs signals $V_{sp}$ and $V_{sn}$. The HPF 501 removes low-frequency noise included in the induced signal. Thus, a more accurate impedance measuring result may be obtained.

The capacitor 103 receives a voltage signal output from the HPF 501. The capacitor 103 includes capacitors 221 and 223 respectively corresponding to the output signals $V_{sp}$ and $V_{sn}$ which are differential signals. The capacitors 221 and 223 remove DC components from the output signals $V_{sp}$ and $V_{sn}$, respectively, and output signals $V_{ip}$ and $V_{in}$.

The controller outputs a control signal $f_{rstp}$ to turn on or off the switch 107 based on whether the voltage value of the induced signal is included in a threshold range. The switch 107 includes switches 225 and 227 respectively corresponding to the output signals $V_{sp}$ and $V_{sn}$ which are the differential signals. The switch 107 determines whether to set, to be a reference voltage value, voltage values of the voltage signals $V_{ip}$ and $V_{in}$ output from the capacitor 103 based on the control signal $f_{rstp}$. The switches 225 and 227 may be set to be turned on or off based on the control signal $fr_{stp}$. When the control signal $f_{rstp}$ is H, the switches 225 and 227 may be set to be on, and the output signals $V_{ip}$ and $V_{in}$ may be set to be a reference voltage value $V_{com}$ irrespective of the output signals $V_{sp}$ and $V_{sn}$. When the control signal $f_{rstp}$ is L, the switches 225 and 227 may be set to be off, and the output signals $V_{ip}$ and $V_{in}$ may follow the output signals $V_{sp}$ and $V_{sn}$ based on the reference voltage value $V_{com}$.

In an example, the impedance measuring apparatus may further include a signal processor 109 as described above with reference to FIG. 2. According to an example, the signal processor 109 may include an amplifier 241, a demodulator 243, a peak detector 245, an LPF 247, an ADC (not shown), or any combinations thereof. For the detailed description of a structure and an operation of the signal processor 109, reference may be made to the description provided above with reference to FIG. 2.

Figure 6:
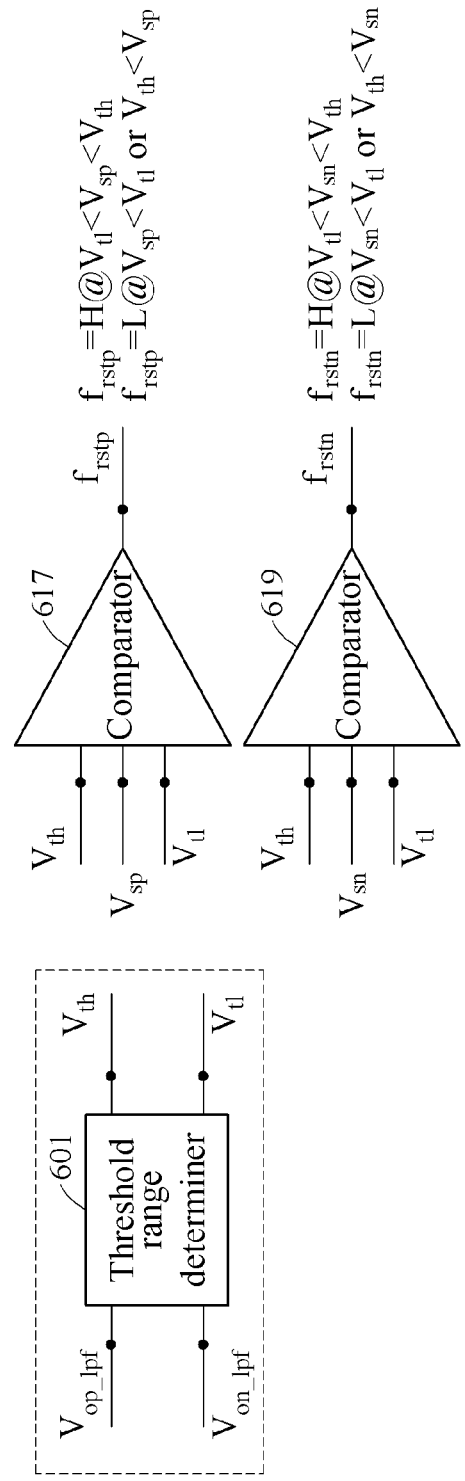
FIG. 6 is a diagram illustrating an example of a detailed configuration of an impedance measuring apparatus.

FIG. 6 is a diagram illustrating an example of a detailed configuration of an impedance measuring apparatus.

Referring to FIG. 6, an impedance measuring apparatus includes a capacitor, a controller, a switch, and a threshold range determiner 601, for example. The capacitor receives induced signals $V_{sp}$ and $V_{sn}$ determined by an impedance of a measurement target. The controller outputs a control signal $f_{rstp}$ to turn on or off the switch based on whether voltage values of the induced signals $V_{sp}$ and $V_{sn}$ are included in a threshold range.

The threshold range determiner 601 determines the threshold range based on whether an output signal satisfies a preset condition. The threshold range determiner 601 determines the threshold range based on whether a voltage value of the output signal satisfies the preset condition.

In an example, the output signal may include voltage signals $V_{ip}$ and $V_{in}$ output from the capacitor. The threshold range determiner 601 may determine the threshold range based on whether the voltage signals $V_{ip}$ and $V_{in}$ output from the capacitor satisfy the preset condition. The threshold range may be determined based on a first threshold voltage value $V_{th}$ and a second threshold voltage value $V_{tl}$.

In an example, the threshold range determiner 601 may include a signal processor. The signal processor may perform signal processing on voltage signals $V_{ip}$ and $V_{in}$ transferred from a node to which the switch and the capacitor are connected. An output signal to be input to the threshold range determiner 601 may include voltage signals $V_{op\_lpf}$ and $V_{on\_lpf}$ output from the signal processor. The threshold range determiner 601 may determine the threshold range based on whether the voltage signals $V_{op\_lpf}$ and $V_{on\_lpf}$ output from the signal processor satisfy the preset condition.

Comparators 617 and 619 may receive the first threshold voltage value $V_{th}$ and the second threshold voltage value $V_{tl}$ to define the voltage values of the induced signals $V_{sp}$ and $V_{sn}$ and the threshold range. The threshold range of the comparators 617 and 619 may be set based on the first threshold voltage value $V_th$ and the second threshold voltage value $V_{tl}$. The comparators 617 and 619 compare the voltage values of the induced signals $V_{sp}$ and $V_{sn}$ to each of the first threshold voltage value $V_{th}$ and the second threshold voltage value $V_{tl}$, and set the control signal $f_{rstp}$ to be H or L based on whether the induced signal $V_{sp}$ is between the first threshold voltage value $V_{th}$ and the second threshold voltage value $V_{tl}$. The switch determines whether to set, to be a reference voltage value, a voltage value of a voltage signal output from the capacitor based on the control signal $f_{rstp}$.

FIGS. 7A through 7D are diagrams illustrating examples of a signal processor of FIGS. 2 through 5 including an ADC.

Figure 7A:
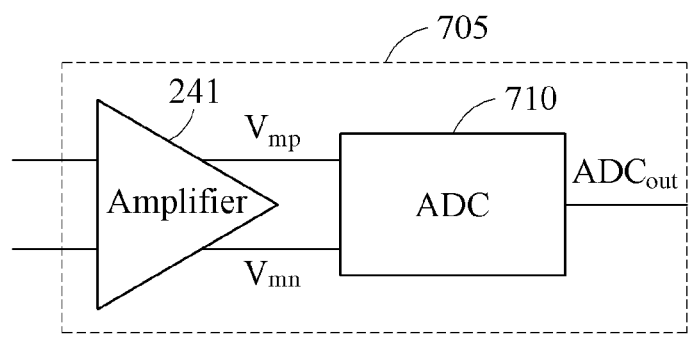
FIGS. 7A through 7D are diagrams illustrating examples of a signal processor of FIGS. 2 through 5 including an analog-to-digital converter (ADC).

Referring to FIG. 7A, a signal processor 705 includes an amplifier 241 and an ADC 710 connected to the amplifier 241. The amplifier 241 amplifies an input signal to output signals $V_{mp}$ and $V_{mn}$. The ADC 710 converts the input signal which is an analog signal to a digital signal $ADC_{out}$ and outputs the digital signal $ADC_{out}$ corresponding to the input signal. For example, the ADC 710 may extract a signal value from an analog signal at regular intervals through signal sampling, and represent the extracted signal value by numerical values, for example, binarize the extracted signal value, through quantization. In the example of FIG. 7A, the ADC 710 performs digital conversion on the signals $V_{mp}$ and $V_{mn}$ output from the amplifier 241.

Figure 7B:
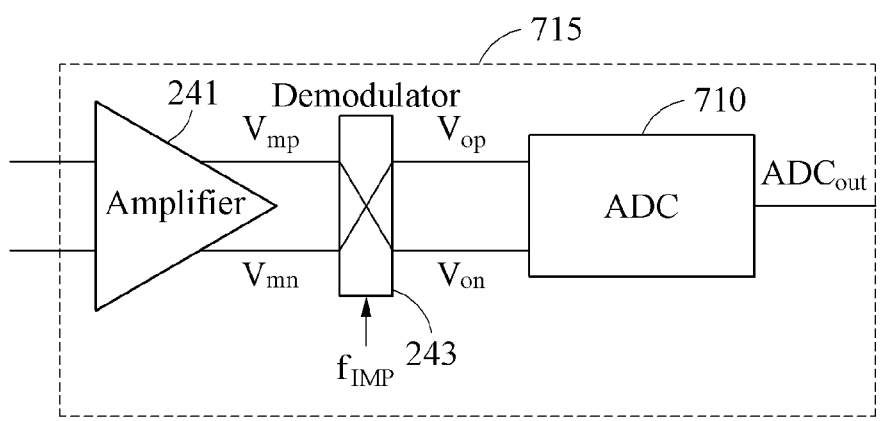

Referring to FIG. 7B, a signal processor 715 includes an amplifier 241, a demodulator 243 connected to the amplifier 241, and an ADC 710 connected to the demodulator 243. The demodulator 243 demodulates signals $V_{mp}$ and $V_{mn}$ output from the amplifier 241 and outputs demodulated signals $V_{op}$ and $V_{on}$. The ADC 710 converts the demodulated signals $V_{op}$ and $V_{on}$ output from the demodulator 243 to a digital signal $ADC_{out}$ and outputs the digital signal $ADC_{out}$.

Figure 7C:
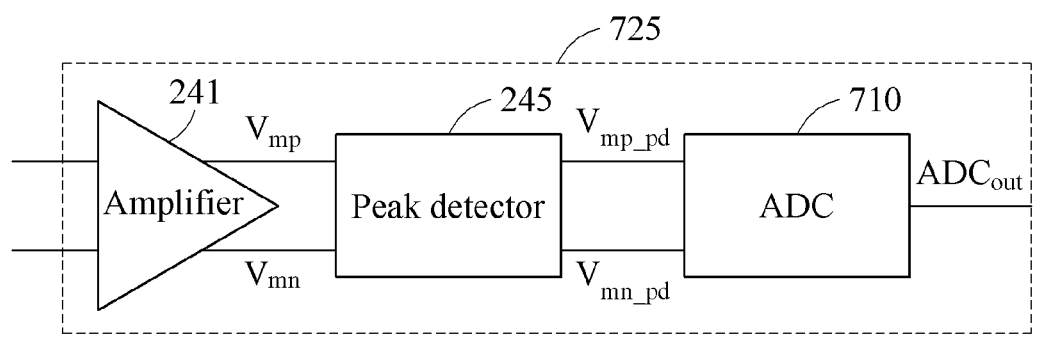

Referring to FIG. 7C, a signal processor 725 includes an amplifier 241, a peak detector 245 connected to the amplifier 241, and an ADC 710 connected to the peak detector 245. The peak detector 245 detects peaks of signals $V_{mp}$ and $V_{mn}$ output from the amplifier 241 and outputs signals $V_{mp\_pd}$ and $V_{mn\_pd}$. The ADC 710 converts the signals $V_{mp\_pd}$ and $V_{mn\_pd}$ output from the peak detector 245 to a digital signal $ADC_{out}$ and outputs the digital signal $ADC_{out}$.

Figure 7D:
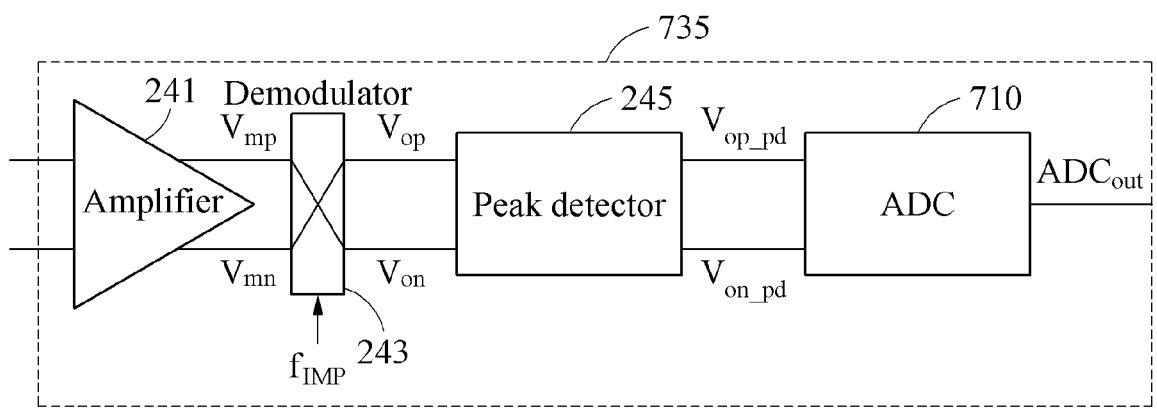

Referring to FIG. 7D, a signal processor 735 includes an amplifier 241, a demodulator 243 connected to the amplifier 241, a peak detector 245 connected to the demodulator 243, and an ADC 710 connected to the peak detector 245. The demodulator 243 demodulates signals $V_{mp}$ and $V_{mn}$ output from the amplifier 241 and outputs demodulated signals $V_{op}$ and $V_{on}$. The peak detector 245 detects peaks of the demodulated signals $V_{op}$ and $V_{on}$ output from the demodulator 243 and outputs signals $V_{op\_pd}$ and $V_{on\_pd}$. The ADC 710 converts the signals $V_{op\_pd}$ and $V_{on\_pd}$ output from the peak detector 245 to a digital signal $ADC_{out}$ and outputs the digital signal $ADC_{out}$.

In another example, an LPF may be provided at an input end of the ADC 710 of FIGS. 7A through 7D. In this example, the ADC 710 may convert a signal obtained through filtering performed by the LPF to a digital signal.

Figure 8:
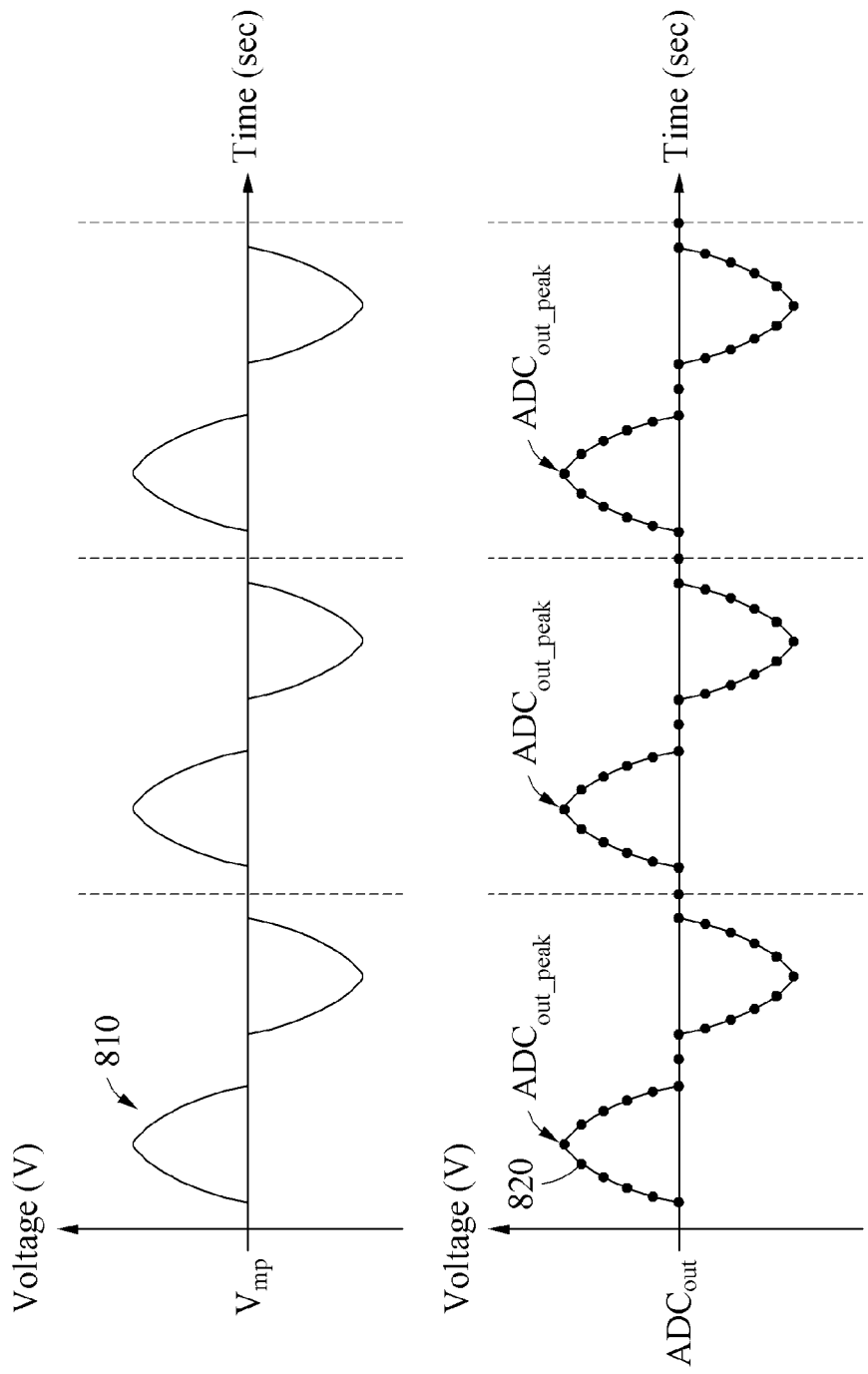
FIG. 8 is a diagram illustrating an example of an output signal of an ADC.

FIG. 8 is a diagram illustrating an example of an output signal of an ADC.

FIG. 8 illustrates a graph 810 of a waveform of the signal $V_{mp}$ output from the amplifier 241 of the signal processor 705 of FIG. 7A, and illustrates the signal $ADC_{out}$ output from the ADC 710. In an example, the ADC 710 may perform signal sampling on the signal $V_{mp}$ input to the ADC 710 to extract sampled signal values 820 of the signal $V_{mp}$ at regular intervals, and binarize the signal values 820 and generate a digital signal. A peak value $ADC_{out\_peak}$ of the generated digital signal may thus be readily extracted.

Figure 9A:
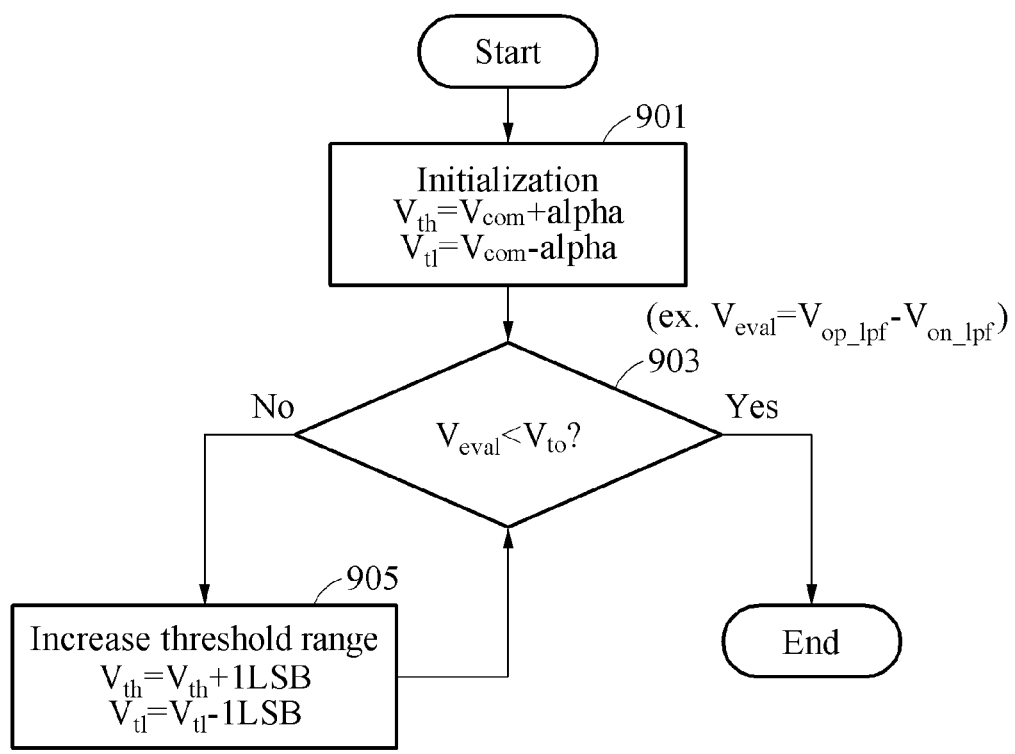
FIG. 9A is a flowchart illustrating an example of an operation of the impedance measuring apparatus.

FIG. 9A is a flowchart illustrating an example of an operation of an impedance measuring apparatus. For ease of explanation, explanations of FIG. 9A will be made with reference to the impedance measuring apparatus of FIG. 6.

Referring to FIG. 9A, in operation 901, the threshold range determiner 601 initializes a threshold range. The threshold range determiner 601 may set initial values of a first threshold voltage value $V_{th}$ and a second threshold voltage value $V_{tl}$ using a reference voltage value $V_{com}$ and an initial voltage interval (alpha). For example, the threshold range determiner 601 may set a sum of the reference voltage value $V_{com}$ and the initial voltage interval (alpha) to be the first threshold voltage value $V_{th}$ and a difference between the reference voltage value $V_{com}$ and the initial voltage interval (alpha) to be the second threshold voltage value $V_{tl}$.

The threshold range determiner 601 may process an input signal and compare a magnitude $V_{eval}$ of an output signal and a preset value $V_{to}$ to adjust the first threshold voltage value $V_{th}$ or the second threshold voltage value $V_{to}$. In operation 903, the threshold range determiner 601 determines whether the output signal satisfies a preset condition. The threshold range determiner 601 may process the input signal and compare the output value $V_{eval}$ and the preset value $V_{to}$. For example, the threshold range determiner 601 may receive two output signals to calculate the output value $V_{eval}$ or receive a single output signal to calculate the output value $V_{eval}$. For example, the input signal of the threshold range determiner 601 may include output signals $V_{op\_lpf}$ and $V_{on\_lpf}$ of the LPF 247, output signals $V_{op\_pd}$ and $V_{on\_pd}$ of the peak detector 245, or a signal in any operations or stages described above with reference to FIG. 2. The threshold range determiner 601 may perform an additional process on the input signal, for example, by changing a scale to obtain the output value $V_{eval}$. Such operations or functions of the threshold range determiner 601 may also be performed by a digital processor.

In operation 905, in response to the output signal not satisfying the preset condition, the threshold range determiner 601 increases the threshold range. The threshold range determiner 601 may set a first threshold voltage value $V_{th}$ and a second threshold voltage value $V_{tl}$ to be newly tested, using the first threshold voltage value $V_{th}$ and the second threshold voltage value $V_{tl}$, and a unit voltage interval, such as the least significant bit [LSB]. For example, the threshold range determiner 601 may set a sum of the current first threshold voltage value $V_{th}$ and the unit voltage interval (LSB) to be the next first threshold voltage value $V_{th}$, and a difference between the current second threshold voltage value $V_{tl}$ and the unit voltage interval (LSB) to be the next second threshold voltage value $V_{tl}$. In response to the output signal satisfying the preset condition, the threshold range determiner 601 may set the threshold range using the first threshold voltage value $V_{th}$ and the second threshold voltage value $V_{tl}$.

As described above, the threshold range determiner 601 may rapidly determine the threshold range using a set unit voltage interval (LSB).

The threshold range determiner 601 may successively perform the operations described above with reference to FIG. 9A, or perform the operations at predetermined time intervals. The threshold range determiner 601 may reset a first threshold voltage value $V_{th}$ and a second threshold voltage value $V_{tl}$, after a predetermined time interval elapses after setting the first threshold voltage value $V_{th}$ and the second threshold voltage value $V_{tl}$. The threshold range determiner 601 may determine whether to set the threshold range based on the number of times when the output value $V_{eval}$ exceeds the preset value $V_{to}$. For example, in a case in which the output value $V_{eval}$ exceeds the preset value $V_{tl}$, once or more than a preset number of times, the threshold range determiner 601 may perform the operations described above with reference to FIG. 9A.

Figure 9B:
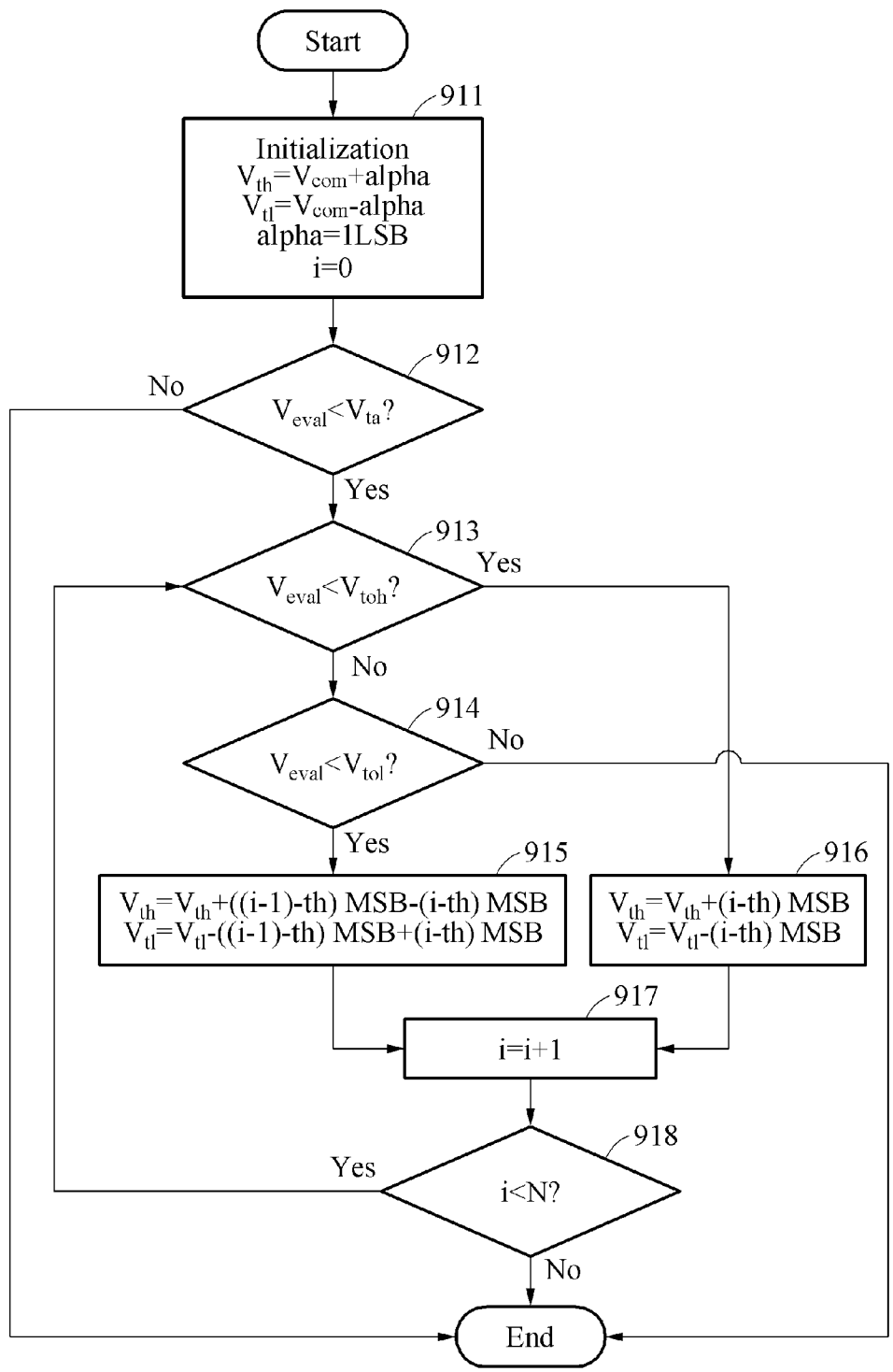
FIG. 9B is a flowchart illustrating an example of an operation of the impedance measuring apparatus.

FIG. 9B is a flowchart illustrating an example of an operation of an impedance measuring apparatus. For ease of explanation, explanations of FIG. 9B will be made with reference to the impedance measuring apparatus of FIG. 6.

Referring to FIG. 9B, in operation 911, the threshold range determiner 601 initializes a threshold range. The threshold range determiner 601 may set initial values of a first threshold voltage value $V_{th}$ and a second threshold voltage value $V_{tl}$ using a reference voltage value $V_{com}$ and an initial voltage interval (alpha). For example, the threshold range determiner 601 may set a sum of the reference voltage value $V_{com}$ and the initial voltage interval (alpha) to be the first threshold voltage value $V_{th}$ and a difference between the reference voltage value $V_{com}$ and the initial voltage interval (alpha) to be the second threshold voltage value $V_{tl}$. The initial voltage interval (alpha) may be a unit voltage interval (LSB) described above with reference to FIG. 9A. The threshold range determiner 601 may initialize a count i to be 0.

The threshold range determiner 601 may determine an optimal threshold range such that an output signal is included in the threshold range through a binary weighted search. The threshold range determiner 601 may determine the threshold range using a variable voltage interval (most significant bit [MSB]) instead of using a fixed voltage interval (LSB). The variable voltage interval (MSB) may be set to be smaller as the count i increases. Thus, the threshold range determiner 601 may determine the threshold range more accurately by gradually reducing the variable voltage interval (MSB).

For example, an i-th variable voltage interval, or an i-th MSB, may be 0.5 times an (i−1)th variable voltage interval, or a (i−1)th MSB, but not limited thereto. A ratio between the i-th variable voltage interval and the (i−1)th variable voltage interval may be set to be various values between 0 and 1.

In operation 912, the threshold range determiner 601 determines whether a state is a measurement state. For example, in response to a measured value $V_{eval}$ being greater than a preset reference value $V_{ta}$, the threshold range determiner 601 may determine that the state is the measurement state in which measurement is being performed. In response to the measured value $V_{eval}$ being less than the preset reference value $V_{ta}$, the threshold range determiner 601 may determine that the state is not the measurement state, or that the state is a non-measurement state. Herein, the measured value $V_{eval}$ may be a difference between voltage signals $V_{op\_Ipf}$ and $V_{on\_Ipf}$ output from a signal processor, and the non-measurement state may include a state in which an impedance measurement target and an electrode interface are not desirably connected, or current is not applied even though the electrode interface is desirably connected. In the non-measurement state, a signal to be input to the comparator 105 of FIG. 2 may be included in a threshold range including $V_{th}$ and $V_{tl}$, the switch 107 of FIG. 2 may be short-circuited, and an input value of the amplifier 241 of FIG. 2 may become $V_{com}$. Thus, the measured value $V_{eval}$ may be a magnitude of a noise level. Thus, by setting the reference value $V_{ta}$ to be appropriate, whether to change a set threshold value may be determined.

In operations 913 and 914, the threshold range determiner 601 determines whether the output value $V_{eval}$ overshoots or undershoots. The threshold range determiner 601 may determine whether an output signal of the impedance measuring apparatus satisfies a preset condition. The threshold range determiner 601 may compare, to preset values $V_{toh}$ and $V_{tol}$, the output value $V_{eval}$ which is a difference value between differential signals included in the output signal. In operation 916, in response to the output value $V_{eval}$ being greater than the preset value $V_{toh}$, the threshold range determiner 601 increases the preset value $V_{toh}$ to decrease the output value $V_{eval}$. In operation 915, in response to the output value $V_{eval}$ being less than the preset value $V_{tol}$, the threshold range determiner 601 decreases the preset value $V_{tol}$ to increase the output value $V_{eval}$. Herein, when the output value $V_{eval}$ is in a range less than the upper value $V_{toh}$ and greater than the lower value $V_{tol}$, the threshold range determiner 601 may determine that the threshold range is set appropriately, and thus terminate the determining of the threshold range.

In operation 916, the threshold range determiner 601 increases the threshold range. The threshold range determiner 601 may set a first threshold voltage value $V_{th}$ and a second threshold voltage value $V_{tl}$ to be newly tested, using the first threshold voltage value $V_{th}$, the second threshold voltage value $V_{tl}$, and the i-th variable voltage interval (i-th MSB). For example, the threshold range determiner 601 may set a sum of the current first threshold voltage value $V_{th}$ and the i-th variable voltage interval (i-th MSB) to be the next first threshold voltage value $V_{th}$, and a difference between the current second threshold voltage value $V_{tl}$ and the i-th variable voltage interval (i-th MSB) to be the next second threshold voltage value $V_{tl}$. In operation 917, the threshold range determiner 601 increases the count i by 1.

In operation 915, the threshold range determiner 601 decreases the threshold range. The threshold range determiner 601 may set a first threshold voltage value $V_{th}$ and a second threshold voltage value $V_{tl}$ to be newly tested, using the first threshold voltage value $V_{th}$, the second threshold voltage value $V_{tl}$, the i-th variable voltage interval (i-th MSB), and the (i−1)th variable voltage interval ((i−1)th MSB). For example, the threshold range determiner 601 may set, to be the next first threshold voltage value $V_{th}$, a value obtained by subtracting, from the current first threshold voltage value $V_{th}$, a difference between the i-th variable voltage interval (i-th MSB) and the (i−1)th variable voltage interval ((i−1)th MSB). The threshold range determiner 601 may set, to be the next second threshold voltage value $V_{tl}$, a value obtained by adding, to the current first threshold voltage value $V_{th}$, the difference between the i-th variable voltage interval (i-th MSB) and the (i−1)th variable voltage interval. In operation 917, the threshold range determiner 601 increases the count i by 1.

In operation 918, the threshold range determiner 601 repeats the determining of a threshold value when the count i is less than a limited number N of times. The threshold range determiner 601 may determine whether a termination condition is satisfied based on the count i. The threshold range determiner 601 may prevent an infinite loop by limiting the count i to a value less than the limited number N of times.

Figure 10:
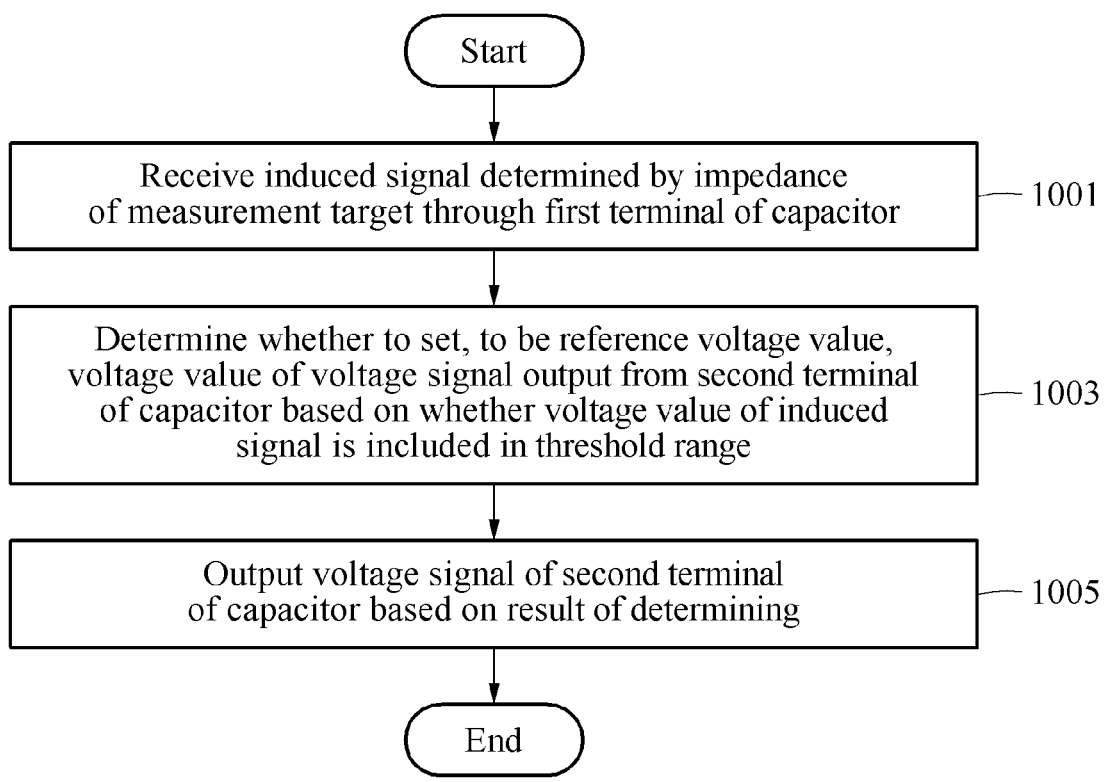
FIG. 10 is a flowchart illustrating an example of an impedance measuring method.

FIG. 10 is a flowchart illustrating an example of an impedance measuring method. The impedance measuring method to be described hereinafter with reference to FIG. 10 may include any, any combination, or all operations discussed above, and may also be performed by an impedance measuring apparatus described above with reference to FIGS. 1 through 9B, as a non-limiting example.

Referring to FIG. 10, in operation 1001, the impedance measuring apparatus receives, through a first terminal of a capacitor, an induced signal determined by an impedance of a measurement target. The induced signal may include impedance characteristics of a body which is the measurement target. The impedance measuring apparatus may measure an impedance of the body, or a body impedance, by combining information associated with an applied current and information extracted from the induced signal.

In operation 1003, the impedance measuring apparatus determines whether to set a voltage value of a second terminal of the capacitor to be a reference voltage value based on whether a voltage value of the induced signal is included in a threshold range. The capacitor may remove a DC component from the induced signal. In response to the voltage value of the induced signal being in the threshold range, the impedance measuring apparatus may determine the voltage value to be unnecessary for impedance measurement, and output the reference voltage value. Conversely, in response to the voltage value of the induced signal being out of the threshold range, the impedance measuring apparatus may determine the voltage value to be necessary for impedance measurement, and output the voltage value.

In operation 1005, the impedance measuring apparatus outputs the voltage signal of the second terminal of the capacitor based on a result of the determining. The impedance measuring apparatus may perform signal processing on the voltage signal of the second terminal of the capacitor. The impedance measuring apparatus may perform amplification, phase adjustment, peak detection, smoothness, and digital conversion on the voltage signal output from the second terminal of the capacitor. The impedance measuring apparatus may measure the body impedance using the information associated with the applied current and an output value obtained by the digital conversion.

In an example, the impedance measuring apparatus may perform signal processing on the voltage signal of the second terminal of the capacitor. The impedance measuring apparatus may amplify the voltage signal of the second terminal of the capacitor, detect a peak of the voltage signal of the second terminal of the capacitor, or perform low-pass filtering on a voltage signal output from a peak detector based on the detected peak.

Figure 11:
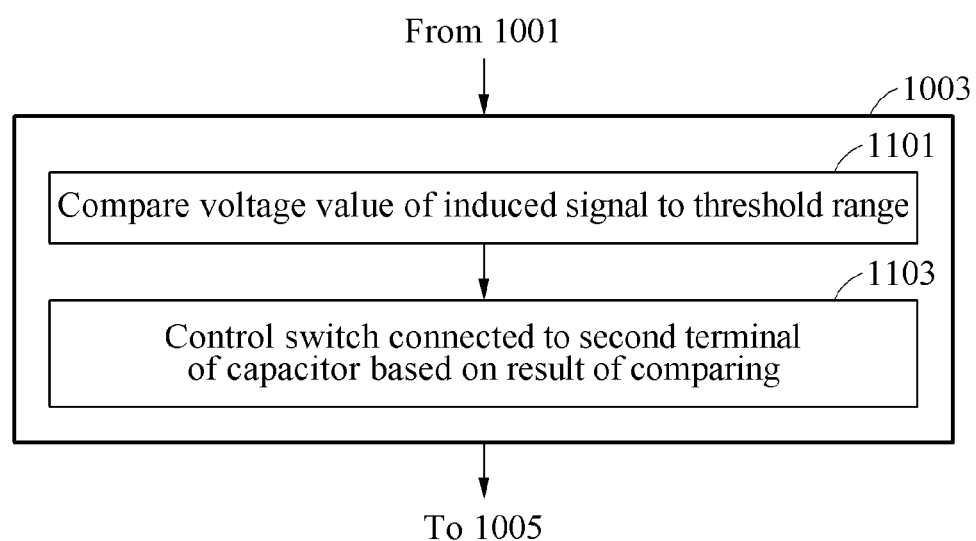
FIG. 11 is a flowchart illustrating an example of a switch controlling method.

FIG. 11 is a flowchart illustrating an example of a switch controlling method.

Operation 1003 described above with reference to FIG. 10 may include operations 1101 and 1103 to be described hereinafter with reference to FIG. 11. Referring to FIG. 11, in operation 1101, an impedance measuring apparatus compares, to a threshold range, a voltage value of an induced signal received through a first terminal of a capacitor of the impedance measuring apparatus.

In operation 1103, the impedance measuring apparatus controls a switch connected to a second terminal of the capacitor based on a result of the comparing. In response to the voltage value of the induced signal being in the threshold range, the impedance measuring apparatus may output a first control signal to turn on the switch. Conversely, in response to the voltage value of the induced signal being out of the threshold range, the impedance measuring apparatus may output a second control signal to turn off the switch.

Herein, the switch may be connected to a reference voltage source. The impedance measuring apparatus may turn on the switch using the first control signal and output a reference voltage value. The impedance measuring apparatus may turn off the switch using the second control signal and output a voltage signal output from the second terminal of the capacitor.

The impedance measuring apparatus 100, the capacitor 103, 403, the controller 105, the switch 107, 407, the signal processor 109, the comparator 411, 617, 619 the control signal adjuster 413, the peak detector 445, the low power filter 447, and the threshold range determiner 601 described herein with respect to FIGS. 1-11 are implemented by hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-11 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An impedance measuring apparatus, comprising:
   one or more capacitors configured to receive an induced signal determined by an impedance of a measurement target;
   a controller configured to output a control signal to selectively turn a switch on or off based on whether a voltage value of the induced signal is included in a threshold range; and
   the switch configured to determine whether to set, to be a reference voltage value, a voltage value of a capacitor voltage signal output from the one or more capacitors based on the control signal.

2. The impedance measuring apparatus of claim 1, wherein, in response to the voltage value of the induced signal being in the threshold range, the controller is configured to output a first control signal to turn on the switch; and
   in response to the voltage value of the induced signal being out of the threshold range, the controller is configured to output a second control signal to turn off the switch.

3. The impedance measuring apparatus of claim 1, wherein the controller comprises:
   a comparator configured to
   receive a first threshold voltage value and a second threshold voltage value to define the voltage value of the induced signal and the threshold range, and
   compare the voltage value of the induced signal to each of the first threshold voltage value and the second threshold voltage value.

4. The impedance measuring apparatus of claim 1, wherein a first terminal of the switch is connected to the one or more capacitors, and a second terminal of the switch is connected to a terminal configured to provide the reference voltage value.

5. The impedance measuring apparatus of claim 1, further comprising:
   a signal processor configured to perform signal processing on the capacitor voltage signal transferred from a node to which the switch and the one or more capacitors are connected.

6. The impedance measuring apparatus of claim 5, wherein the signal processor comprises:
a demodulator configured to adjust a frequency band of the capacitor voltage signal transferred to an input terminal of the signal processor;
a peak detector configured to detect a peak from a demodulated voltage signal output from the demodulator; and
a low-pass filter (LPF) configured to perform low-pass filtering on a peak-detected voltage signal output from the peak detector based on the detected peak.

7. The impedance measuring apparatus of claim 6, wherein the signal processor further comprises:
an amplifier disposed between the node and the demodulator, and configured to amplify the capacitor voltage signal transferred from the node.

8. The impedance measuring apparatus of claim 6, wherein the signal processor further comprises:
an analog-to-digital converter (ADC) configured to convert the capacitor voltage signal from the amplifier, the demodulated voltage signal output from the demodulator or the peak-detected voltage a signal output from the peak detector to a digital signal.

9. The impedance measuring apparatus of claim 1, further comprising:
a current source configured to supply current of a predefined frequency to the measurement target; and
a high-pass filter (HPF) configured to perform high-pass filtering on the induced signal determined by the impedance of the measurement target.

10. An impedance measuring apparatus, comprising:
one or more capacitors configured to receive an induced signal determined by an impedance of a measurement target;
a controller configured to output a control signal to selectively turn a switch on or off based on whether a voltage value of the induced signal is included in a threshold range, and control whether to hold the control signal; and
the switch configured to determine whether to set, to be a reference voltage value, a voltage value of a capacitor voltage signal output from the one or more capacitors based on the control signal.

11. The impedance measuring apparatus of claim 10, wherein the controller comprises:
a control signal adjuster configured to output a control signal in response to an input signal, and hold the output control signal irrespective of an input signal during a predetermined time interval.

12. An impedance measuring apparatus, comprising:
one or more capacitors configured to receive an induced signal determined by an impedance of a measurement target;
a controller configured to output a control signal to selectively turn a switch on or off based on whether a voltage value of the induced signal is included in a threshold range, and control whether to hold the control signal;
the switch configured to determine whether to set, to be a reference voltage value, a voltage value of a capacitor voltage signal output from the one or more capacitors based on the control signal; and
a threshold range determiner configured to determine the threshold range based on whether the capacitor voltage signal output from the one or more capacitors satisfies a preset condition.

13. The impedance measuring apparatus of claim 12, wherein, in response to the capacitor voltage signal output from the one or more capacitors being out of the threshold range, the threshold range determiner is configured to increase the threshold range by a unit interval of the threshold range, and determine whether the capacitor voltage signal output from the one or more capacitors is in the increased threshold range.

14. The impedance measuring apparatus of claim 12, wherein, in response to the capacitor voltage signal output from the one or more capacitors being out of a first set range, the threshold range determiner is configured to increase the threshold range, and
in response to the capacitor voltage signal output from the one or more capacitors being in a second set range, the threshold range determiner is configured to decrease the threshold range.

15. The impedance measuring apparatus of claim 12, further comprising:
a signal processor configured to perform signal processing on a voltage signal transferred from a node to which the switch and the one or more capacitors are connected.

16. An impedance measuring method to be performed by an impedance measuring apparatus, comprising:
receiving, through a first terminal of a capacitor, an induced signal to be determined by an impedance of a measurement target;
determining whether to set a voltage value of a capacitor voltage signal output from a second terminal of the capacitor to be a reference voltage value based on whether a voltage value of the induced signal is included in a threshold range; and
outputting the capacitor voltage signal of the second terminal of the capacitor based on a result of the determining.

17. The impedance measuring method of claim 16, wherein the determining comprises:
comparing the voltage value of the induced signal to the threshold range; and
controlling a switch connected to the second terminal of the capacitor based on a result of the comparing.

18. The impedance measuring method of claim 17, wherein the controlling comprises:
in response to the voltage value of the induced signal being included in the threshold range, outputting a first control signal to turn on the switch; and
in response to the voltage value of the induced signal not being included in the threshold range, outputting a second control signal to turn off the switch.

19. The impedance measuring method of claim 16, further comprising:
performing signal processing on the capacitor voltage signal of the second terminal of the capacitor.

20. The impedance measuring method of claim 19, wherein the performing of the signal processing comprises:
amplifying the capacitor voltage signal of the second terminal of the capacitor.

21. The impedance measuring method of claim 19, wherein the performing of the signal processing comprises:
adjusting a frequency band of the capacitor voltage signal of the second terminal of the capacitor.

22. The impedance measuring method of claim 19, wherein the performing of the signal processing comprises:
detecting a peak from the capacitor voltage signal of the second terminal of the capacitor; and performing low-pass filtering on a peak-detected voltage signal output from a peak detector based on the detected peak.

\* \* \* \* \*